(12) United States Patent
Keeler

(10) Patent No.: US 9,899,017 B2
(45) Date of Patent: Feb. 20, 2018

(54) MODULAR ACOUSTIC SOUND PROCESSOR

(71) Applicant: Richard Keeler, Gardena, CA (US)

(72) Inventor: Richard Keeler, Gardena, CA (US)

(*) Notice: Subject to any disclaimer, the term of this patent is extended or adjusted under 35 U.S.C. 154(b) by 0 days.

(21) Appl. No.: 15/209,647

(22) Filed: Jul. 13, 2016

(65) Prior Publication Data

US 2017/0018266 A1 Jan. 19, 2017

Related U.S. Application Data

(60) Provisional application No. 62/191,970, filed on Jul. 13, 2015.

(51) Int. Cl.

| | |
|---|---|
| *G10K 9/20* | (2006.01) |
| *G10K 15/04* | (2006.01) |
| *G10D 3/02* | (2006.01) |
| *G10K 9/22* | (2006.01) |
| *G10K 9/18* | (2006.01) |
| *G10K 15/00* | (2006.01) |
| *G10D 3/00* | (2006.01) |
| *H04R 1/28* | (2006.01) |
| *H04R 25/00* | (2006.01) |
| *A61B 7/02* | (2006.01) |

(52) U.S. Cl.
CPC ............ *G10K 9/22* (2013.01); *G10D 3/02* (2013.01); *G10K 15/04* (2013.01); *A61B 7/02* (2013.01); *H04R 1/2807* (2013.01); *H04R 25/402* (2013.01)

(58) Field of Classification Search
CPC . G10K 9/20; G10K 9/22; G10K 11/04; G10K 11/08; G10K 11/22; G10K 11/002; G10K 15/04; G10K 15/08; G10D 3/02; H04R 1/2807; H04R 1/28
See application file for complete search history.

(56) References Cited

U.S. PATENT DOCUMENTS

| | | | | | |
|---|---|---|---|---|---|
| 1,081,490 | A | * | 12/1913 | Dare | H04R 1/30 181/152 |
| 2,656,004 | A | * | 10/1953 | Olson | H04R 1/22 181/157 |
| 3,157,750 | A | * | 11/1964 | Weingartner | H04R 1/225 181/137 |
| 3,470,979 | A | * | 10/1969 | Everett | F16L 55/02709 181/268 |
| 3,777,844 | A | * | 12/1973 | Johnson | H04R 1/2811 181/199 |
| 3,819,879 | A | * | 6/1974 | Baechtold | H04R 1/225 375/242 |
| 4,064,962 | A | * | 12/1977 | Hunt | F01N 1/02 181/272 |
| 4,142,603 | A | * | 3/1979 | Johnson | G10K 11/04 181/148 |

(Continued)

*Primary Examiner* — Edgardo San Martin
(74) *Attorney, Agent, or Firm* — Inskeep IP Group, Inc.

(57) ABSTRACT

An acoustic sound processor is disclosed, which can be used to modify, enhance, pinpoint, and/or amplify the sound of acoustic instruments, the sound received by a microphone/transducer, or the soundwaves passing through any resonance chamber. The acoustic sound processor includes a plurality of tubes, filters, diaphragms, and collectors with ends that open externally and internally of the sound processor, and other ends that either open to an internal sound collector chamber or bypass the chamber on the opposite side of the device.

11 Claims, 29 Drawing Sheets

(56) References Cited

U.S. PATENT DOCUMENTS

| | | | | |
|---|---|---|---|---|
| 4,189,627 A * | 2/1980 | Flanagan | ................ | H04R 1/22 181/151 |
| 4,231,445 A * | 11/1980 | Johnson | ................ | H04R 1/345 181/148 |
| 4,394,830 A * | 7/1983 | Damiano | ............... | G10D 1/085 84/267 |
| 4,602,245 A * | 7/1986 | Yang | ...................... | G10K 9/122 310/322 |
| 4,632,003 A * | 12/1986 | Kopp | ..................... | G10D 1/085 84/267 |
| 4,823,668 A * | 4/1989 | Marrs | ..................... | G10D 3/02 84/173 |
| 4,852,177 A * | 7/1989 | Ambrose | ............. | H04R 1/1016 181/135 |
| 6,563,033 B1 * | 5/2003 | Porzilli | .................... | G10D 3/02 84/267 |
| 6,587,564 B1 * | 7/2003 | Cusson | .................... | A61B 7/04 181/131 |
| 6,681,661 B2 * | 1/2004 | Lalonde | .................. | G10D 3/02 84/267 |
| 7,259,308 B2 * | 8/2007 | Geiger | ..................... | G10D 3/02 84/267 |
| 7,528,701 B2 * | 5/2009 | Adelman | ................. | G10K 9/00 340/384.7 |
| 7,658,263 B2 * | 2/2010 | Jasnie | .................... | G10K 11/22 123/184.53 |
| 7,674,963 B1 * | 3/2010 | Poggi | ...................... | G10D 3/02 84/312 R |
| 8,340,310 B2 * | 12/2012 | Ambrose | ............. | H04R 1/1016 381/328 |
| 2016/0078779 A1 * | 3/2016 | Sahai | ...................... | A61B 7/02 434/262 |

* cited by examiner

Fig. 1
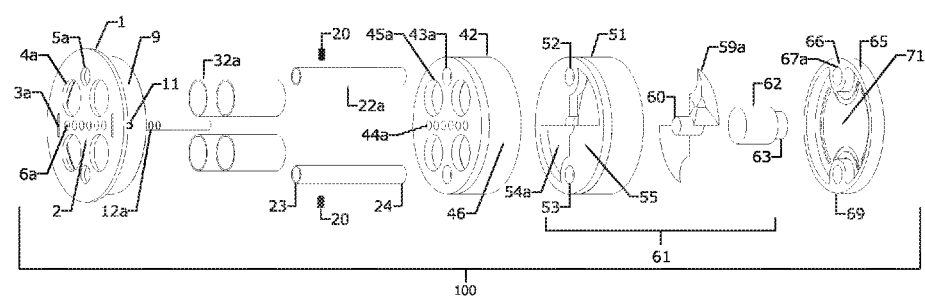
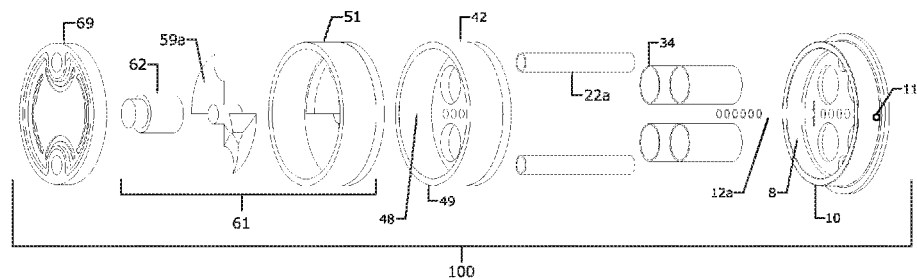

Fig. 5
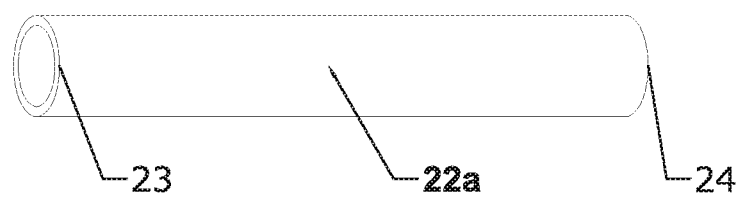
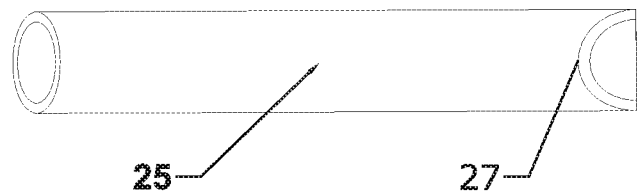
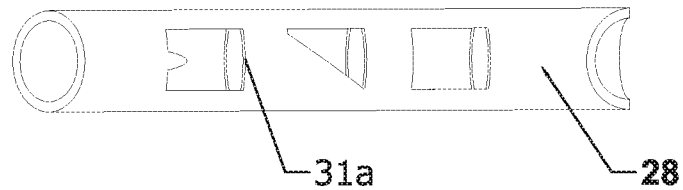

Fig. 6
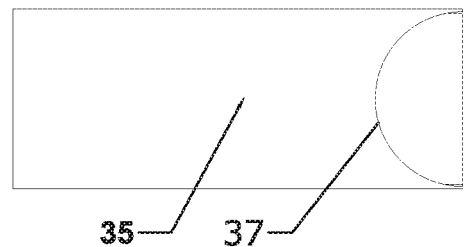
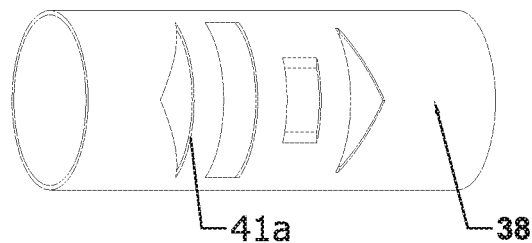

Fig. 7
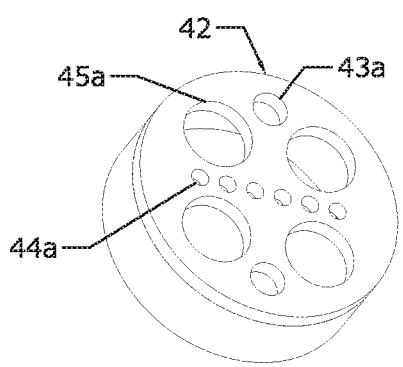
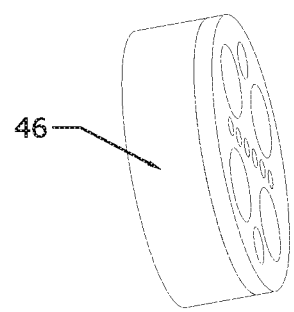
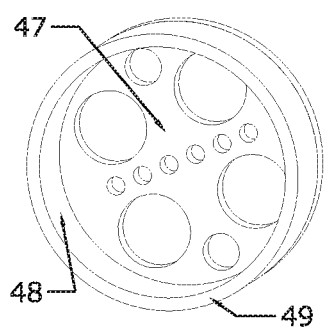

Fig. 19
141 Sound Wave Anti-Reversion Regulator
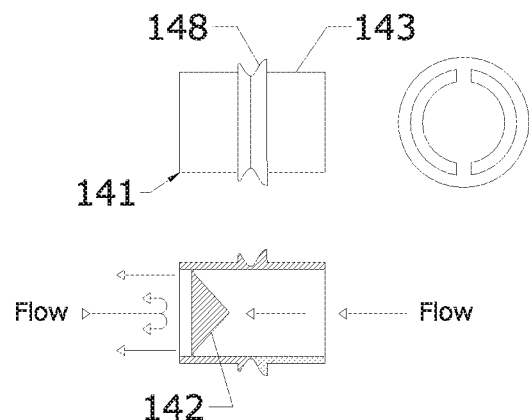
146 Sound Wave Pass Through Regulator
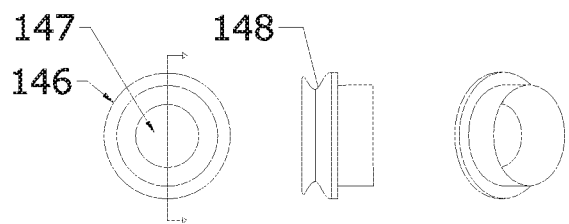
152 Sound Wave Regulator Filter
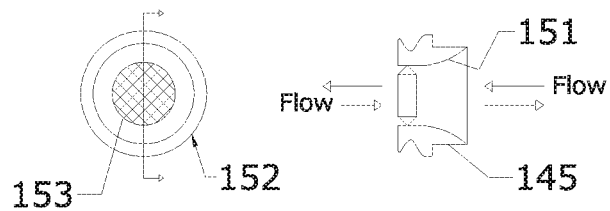

Fig. 20
144 Sound Wave Solid Regulator
Top
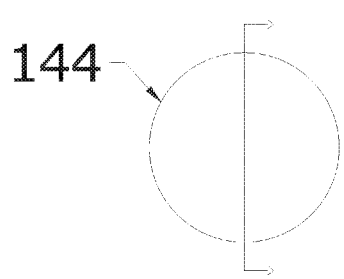
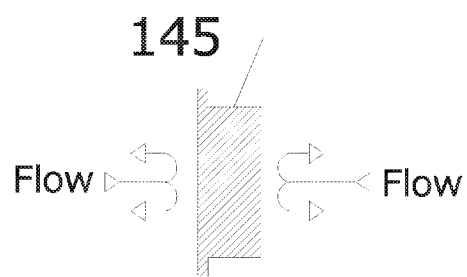

Representation of the Interconnected Systems of the Modular Acoustic Sound Processor

Legend:
- Acoustic Soundwave Intake System
- Acoustic Soundwave Resonance Control System
- Acoustic Soundwave Output System Acoustic Soundwave Intake System Pathway Acoustic Soundwave Resonance Control System Pathway Acoustic Soundwave Output System Pathway

MODULAR ACOUSTIC SOUND PROCESSOR

RELATED APPLICATIONS

This application claims priority to U.S. Provisional Application Ser. No. 62/191,970 filed Jul. 13, 2015 entitled Modular Acoustic Sound Processor, which is hereby incorporated herein by reference in its entirety.

BACKGROUND OF THE INVENTION

This invention relates to the field of acoustic sound processing. It is designed to intake, control, and output sound vibrations, in any embodiment, in any field of use.

When sound waves are produced, the tone can be overwhelmed, limited, or masked by low and/or high overtones or may include undesirable ambient frequencies, causing muddiness, harshness, and feedback. In the field of music recording, for example, this often creates a need for re-tracking or post-production of the sound waves. Broadly, there are two categories of prior art that have attempted to address this problem, especially with regard to acoustic music instruments.

The first category of prior art is a sound hole cover, baffling, plug, or disc, with or without air passages for the resonance chamber. These are designed to reduce feedback by closing the resonance chamber, which chokes air flow or filters and deflects sound waves through the use of screens and panels. Rather than choking airflow to reduce feedback with plugs or using screens and panels as baffles, the modular acoustic sound processor of the present invention seeks to block, control resonance, redirect, align and cancel the input chain of cause and effect in a housed system. This prevents the unwanted sound wave from entering back into the sound source, reducing the regeneration of sound, which interrupts the feedback loop. The modular concept of the present invention allows the various pieces to be used interchangeably to achieve different effects, volume levels, compression, equalization and harmonics, as well as to hold aftermarket products such as wireless systems, bridges, microphones, pickups, cables, etc., as desired by the user. In addition, the adjustable nature of this invention allows the user to tune the resonance of the sound board and the resonance chamber to find and optimize the tone.

The second similar category of prior art to solve the stated problem is sound processing through electronic devices during post production, which admits phase problems, hiss, and noise to the sound signal. The modular sound processor of the present invention processes the sound wave, without the use of electricity. This pre-processing allows the user to create the desired sound prior to transduction. It eliminates unwanted or unnecessary sound signals, such as low end mud, brittle high end, unpleasant overtones, room interference, hiss and noise, prior to amplification.

SUMMARY OF THE INVENTION

The present invention is generally directed to a mechanical acoustic sound processor which houses an interconnected set of systems. It uses specially designed interchangeable component parts to intentionally alter and optimize the harmonic series and overtones of frequencies without the use of electricity, prior to energy transduction. Due to its modular nature, accessories (e.g., rotary vibrato, wireless unit, diaphragm, etc.) can be added or omitted to create the sound desired by the user. The invention can be placed within a preexisting sound chamber (e.g., the chamber of an acoustic guitar), the unit create the sound chamber (e.g., by being positioned over a microphone), or it can be positioned near the location of an external sound. In either application, through changing the air flow rate, geometric volume, and shape of the resonance chamber, the sound pressure, amplitude, transfer rate, and additional sound qualities can be simulated, customized and optimized.

One embodiment of the present invention is directed to an acoustic sound processor for an acoustic instrument, such as a guitar.

Another embodiment of the present invention is directed to an acoustic sound processor that includes the following components: an acoustic soundwave intake system that receives incoming soundwaves, an acoustic soundwave resonance control system pathway that modifies the incoming soundwaves, and an acoustic soundwave output system pathway that outputs the modified soundwaves.

Another embodiment of the present invention is directed to an acoustic sound processor for a microphone, such as a traditionally shaped dynamic microphone or a condenser microphone.

Another embodiment of the present invention is directed to an acoustic sound processor for devices assisting the hearing impaired, such as a hearing aid.

Another embodiment of the present invention is directed to a sound processor that is composed of a top enclosure or sound chassis that is sized to sit at or above a sound hole of an acoustic instrument, a lower enclosure or diaphragm that is positioned so that it is located within the instruments resonance chamber, and an inner enclosure or internal sound collector enclosure that forms an internal sound collector chamber between the enclosure and the diaphragm (or other internal component). The sound collector chamber can have a plurality of tubes of different diameters that connect it to and are in communication with the exterior of the instrument, via apertures in the sound chassis. Further, additional tubes can bypass the sound chamber and the diaphragm, directly connecting the exterior of the guitar to the resonance chamber by extending through the chassis, chamber, and diaphragm. In this respect, the sound processor can allow some soundwaves to pass directly through it, while blocking or modifying others. Additionally, other components can be optionally added to the sound processor, such as a rotary vibrato chassis.

Another embodiment of the present invention is directed to a sound processor that is composed of modular components that can be added or removed by the user. For example, a rotary vibrato, an electronic wireless audio transmission unit, or a diaphragm.

In another embodiment of the present invention, the acoustic sound processor can be included on a variety of sound-based items, such as wind, brass, and acoustic instruments, stethoscopes, surveillance microphones, exhaust systems, noise reduction systems, noise cancellation systems, ultrasound devices, speaker enclosures, scientific sound measuring, and hearing aids.

BRIEF DESCRIPTION OF THE SEVERAL VIEWS OF THE DRAWINGS

These and other aspects, features, and advantages of which embodiments of the invention are capable of will be apparent and elucidated from the following description of embodiments of the present invention, reference being made to the accompanying drawings, in which:

FIG. 1 is an assembled and exploded perspective view, showing the modular and adjustable parts of the present invention, linear design.

FIG. 5 is a side view of the bypass tube variations.

FIG. 6 is a side view of the sound tube variations.

FIG. 7 is three perspective views of the internal sound collector, linear design, including top, side and bottom views.

FIG. 19 includes side, isometric and cross hatch views of sound wave regulator variations.

FIG. 20 is a front and side cross hatch view of a solid sound wave regulator.

DETAILED DESCRIPTION OF THE INVENTION

Figure 2:
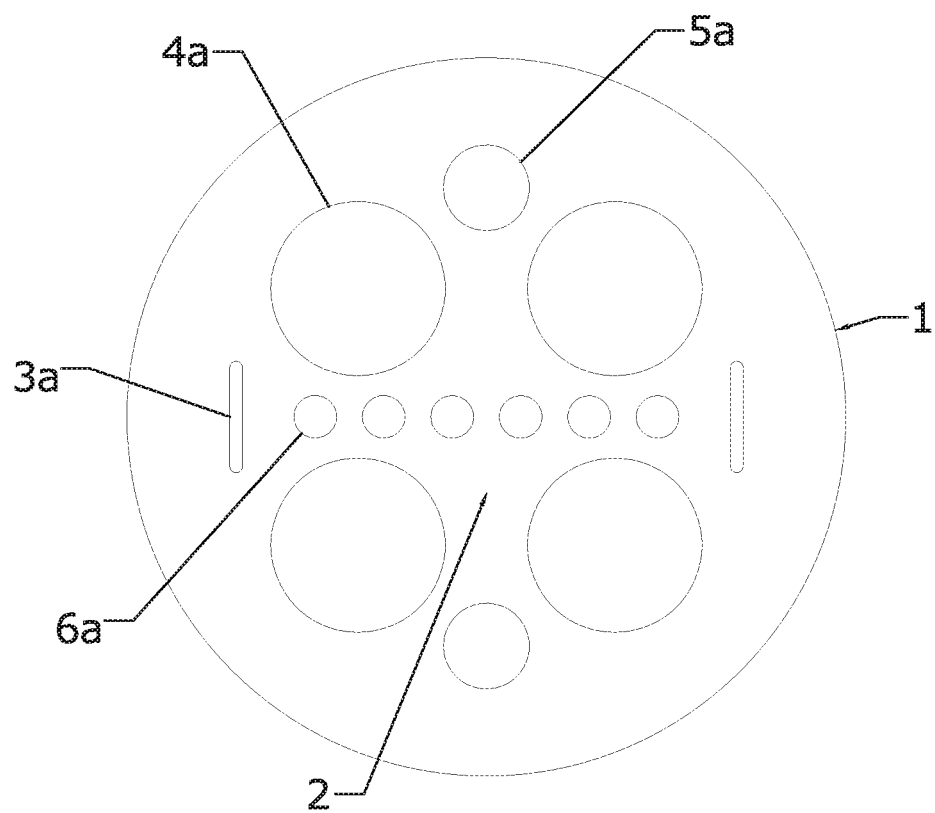
FIG. 2 is a top view of the sound chassis, linear design.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

REFERENCE NUMERALS IN THE DRAWINGS

1 Sound chassis, linear design: Example size between 2.0" to 5.0" in diameter when used in connection with acoustic instruments (e.g., guitar). Can be made of various materials, including metals, composites, plastics, or woods. Typically has a face plate with a plurality of apertures or ports and an outer wall 9 extending generally perpendicularly from the outer perimeter of the face plate.

2 Sound chassis top sound board, linear design: Used to secure 3a, 4a, 5a, 6a.

3a Sound chassis balancing port: Vary in shape and size depending on type of application and embodiment of sound chassis.

4a Sound chassis sound tube mount: Example size range between 0.625" to 1.750" in diameter.

5a Sound chassis bypass tube mount: Example size range between 0.2" to 1.0" in diameter.

6a Sound chassis inline tube mount: Example size range between 0.25" and 0.50" in diameter.

7 Sound chassis cavity, linear design: Example size range between 0.25" to 2.0' in depth.

8 Sound chassis cavity inner wall, linear design: One inner wall per sound chassis 1, example size range between 0.25" to 4.0" deep.

9 Sound chassis outer wall, linear design: One outer wall per sound chassis 1 with an example thickness range between 0.125" and 0.50" and an example depth range between 0.25" and 4.0".

10 Sound chassis support edge, linear design: Example edge ranges between 0.125" to 0.25" in length.

11a Sound chassis mount: This attaches to the sound chassis 1 with, for example, three to ten small tapered grommets (e.g., approximately 0.50" in length and up to 0.5 in diameter).

12a Inline tube: The inline tube is the basic example and can possess any shape such as round, square, rectangular or a custom shape. The tubes usually vary in length between 0.50" to 6.0" and a diameter between 0.20 to 1.0.' The material used varies of different types of metals, composites, plastics, woods.

13 Inline tube, top port of 12a.

14 Inline tube, bottom port of 12a.

15 Inline tube with angle cut: Same as 12a with the addition of angle cut 17 on bottom port of inline tube 4.

17 Bottom port, angle cut of inline tube 15: This cut may vary in degree angles, perpendicular or compound, to the tube 12a surface.

18 Inline tube with side ports: These ports 21a are perpendicular to the surface of the length of the tube.

20 Set screws: The set screws are generally #10-32×¼ inch. The material can be nylon or steel.

21a Inline tube side port: The shape of the side port can vary and the location center line vector points are not always symmetrical to each other.

22a Bypass tube: The straight tube is one example and can possess any cross sectional shape, such as round, square, rectangular, etc. The tubes may vary, for example, in length between 1.0" to 8.0" and in diameter between 0.2" to 1.0".

The material used is preferably of tone quality and varies of different types of metals, composites, plastics, woods.

23 Bypass tube, top port of 22*a*.

24 Bypass tube, bottom port of 22*a*.

25 Bypass tube with angle cut: Same as 22*a* with the addition of angle cut 27 on bottom port of bypass tube.

27 Angle cut of bypass tube 25: The angle cuts may vary in degrees, perpendicular or compound, to the tube.

28 Bypass tube with side ports: These ports 31*a* are perpendicular to the surface of the length of the tube. This type tube may vary in side port numbers, such as between 1-20 per tube.

31*a* Bypass tube side port: The shape of the side port can vary and the location center line vector points are not always symmetrical to each other.

32*a* Sound tube: The tubes may vary in length, for example, between 0.500" to 6.0" and a diameter between 0.200 to 2.5". Example materials include metals, composites, plastics, or woods.

33 Sound tube, top port of 32*a*.

34 Sound tube, bottom port of 32*a*.

35 Sound tube with angle cut: Same as 32*a* with the addition of angle cut 37 on bottom port of sound tube.

37 Angle cut of sound tube 32*a*: The angle cuts may vary in degrees, perpendicular or compound, to the tube.

38 Sound tube with side ports: These ports 41*a* are perpendicular to the surface of the length of the tube 38.

41*a* Sound tube side port: The shape of the side port can vary and the location center line vector points are not always symmetrical to each other.

42 Internal sound collector, summoning junction, or resonance chassis, linear design: Usually between 1.0" to 5.0" in diameter. Can be made of various materials, including metals, composites, plastics, or woods. The sound collector is typically composed of an outer wall 46 extending perpendicularly outward from a face plate of the sound collector so as to form a cavity or resonance chamber 48.

43*a* Internal sound collector bypass tube mount: For example, between 0.2" to 1.0" in diameter.

44*a* Internal sound collector inline tube mount: For example, between 0.25" and 0.5" in diameter.

45*a* Internal sound collector sound tube mount: Range usually between 0.625" to 1.75" in diameter.

46 Internal sound collector outer wall, linear design: One outer wall per sound collector 42 with an example thickness between 0.125" and 0.5" and an example depth between 0.25" and 4.0".

47 Internal sound collector cavity, linear design: For example, between 0.25" to 4.0" in depth.

48 Internal sound collector cavity inner wall, linear design: One inner wall per sound collector 42 between, for example, 0.25" to 4.0" deep.

49 Internal sound collector bottom seal, linear design: One seal area per sound collector 42. For example, between 0.125" and 0.375" in thickness and between 3.0" to 5" in diameter.

51 Rotary vibrato chassis, linear design: For example, between 1.0" to 5.0" in diameter. Example materials include metals, composites, plastics, or woods.

52 Rotary vibrato chassis bypass tube mount: For example, between 0.2" to 1.0" in diameter.

53 Rotary vibrato chassis on/off switch opening: One switch opening per rotary chassis 51. For example, between 0.125" and 0.5" in diameter.

54*a* Rotary vibrato chassis air flow opening, linear design: For example, two to six per rotary chassis 51. Can be of various shapes and sizes.

55 Rotary vibrato chassis top sound board, linear design.

57 Rotary vibrato cavity, linear design.

58 Rotary vibrato blade motor shaft mount, linear design: A cut out with an example diameter that can range between 0.125" and 1.0".

59*a* Rotary vibrato blade, linear design: Can be of various shapes and sizes made of various materials, including metals, composites, plastics, or woods.

60 Rotary vibrato blade motor shaft, linear design.

61 Rotary vibrato, linear design, assembled.

62 Rotary vibrato blade motor, linear design.

63 Rotary vibrato blade motor battery.

64 Set screw threaded cavity: to accommodate #10-32 set screw 20.

65 Diaphragm chassis, linear design: For example, between 1.0" to 5.0" in diameter and between 0.125" and 0.625" in thickness. Can be made of various materials, including metals, composites, plastics, or woods.

66 Diaphragm chassis surface seal, linear design: For example, between 0.125" and 0.375" in thickness and between 1.0" to 5" in diameter.

67*a* Diaphragm chassis bypass tube mount: For example, between 0.2" to 1.0" in diameter.

68 Diaphragm chassis mount edge.

69 Diaphragm unit, linear design, assembled: Chassis 65 with diaphragm 71 installed.

70*a* Diaphragm ports: Size of ports can vary.

71 Diaphragm, linear design: For example, between 1.0" and 6.0" in diameter and a thickness ranging between 0.01" and 0.250". Can be made of various materials, including metals, carbon fiber, composites, plastics or woods.

72 Wireless chassis holder, linear design: For example, between 1.0" to 5.0" in diameter and between 1" and 4" deep. Can be made of various materials, including metals, composites, plastics, or woods.

73*a* Wireless chassis holder bypass tube mount: For example, between 0.2" to 1.0" in diameter.

74 Wireless chassis holder compartment, linear design: For Example, between 1.0" to 5.0" in diameter and can range from 0.5" to 3.0" in depth. Can be made of various materials, including metals, composites, plastics, or woods.

75*a* Wireless chassis holder strap knockouts: Used to feed a Velcro strap to hold the aftermarket wireless transmitter/convex/pickup 76 to the wireless chassis holder 72.

76 Aftermarket wireless transmitter/convex/pickup: This is a generalized reference area representing a wireless transmitter and/or acoustic instrument convex and/or electric guitar pickup.

77 Wireless chassis holder on/off switch opening: For example, between 0.125" and 0.5" in diameter.

85 Acoustic Instrument Example.

86 Acoustic Instrument Sound Board Top.

87 Acoustic Instrument Bridge Assembly.

88 Acoustic Instrument Sound Board Bottom.

89 Acoustic Instrument Resonance Chamber.

90 Acoustic Instrument Sound Hole.

91 Acoustic Instrument Neck.

100 Modular acoustic sound processor, linear design, assembled.

101 Wireless chassis cover, linear design: For example, between 1.0" and 6.0" in diameter and a thickness ranging between 0.01" and 0.25Δ. Can be made of various materials, including metals, carbon fiber, composites, plastics or woods.

102 Wireless cover inline ports: For example, between 0.25" and 0.5" in diameter.

103 Wireless cover sound ports: Range, for example, between 0.625" to 1.75" in diameter.

104 Wireless chassis, linear design: For example, between 2.0" to 5.0" in diameter. Can be made of various materials, including metals, composites, plastics, or woods.

105 Wireless chassis bypass tube mount: Usually between 0.2" to 1.0" in diameter.

106 Wireless chassis cavity inner wall, linear design: For example, measures between 0.25" to 4" deep.

107 Wireless chassis outer wall, linear design: For example, has a thickness between 0.125" and 0.5" and a depth between 0.25" and 4".

108 Wireless modular acoustic sound processor, linear design, assembled.

109 Generic dynamic microphone, assembled.

110 Windscreen, generic dynamic microphone.

111 Electric diaphragm, generic dynamic microphone.

112 Generic dynamic microphone, exploded.

113 Cover, top piece, convex design: For example, a 1.0" to 5.0" radius and 1.0" to 5.0" in length. Can be made of various materials, including metals, composites, plastics, or woods.

114 Cover, bottom piece, convex design: For example, a 1.0" to 5.0" radius and 1.0" to 5.0" in length. Can be made of various materials, including metals, composites, plastics, or woods.

115 Cover transition, top piece, convex design: For example, between 10-45 degrees, a 1.0" to 3.0" radius and 1.0" to 3.0" in length. Can be made of various materials, including metals, composites, plastics, or woods.

116 Cover transition, bottom piece, convex design: For example, between 10-45 degrees, a 1.0" to 3.0" radius and 1.0" to 3.0" in length. Can be made of various materials, including metals, composites, plastics, or woods.

117 Rubber mount holder, top piece, convex design: For example, between 0.5" and 4.0" radius.

118 Rubber mount holder, bottom piece, convex design: Usually between 0.5" and 4.0" radius.

119 Snap lock, upper.

120 Snap lock, lower.

121 Cover, assembled top and bottom, convex design

122 Sound chassis, top, convex design. Usually between 1.0" and 6.0" radius. Can be made of various materials, including metals, composites, plastics, or woods.

123 Sound chassis, bottom, convex design. Usually between 1.0" and 6.0" radius. Can be made of various materials, including metals, composites, plastics, or woods.

124 Sound chassis, assembled top and bottom, convex design.

128 Sound chassis cavity inner wall, convex design: Usually measures between 0.5" to 5.0" deep.

129 Sound chassis inline port, convex design: Vary in diameter between 0.20" and 1.5".

130 Sound chassis diaphragm mount, convex design: Usually between 0.2" to 2.0" in diameter.

132 Diaphragm unit, assembled, convex design: diaphragm chassis 137 with diaphragm 136 installed.

133 Diaphragm ports: Size and shape of the ports can vary.

135 Diaphragm, outer edge, convex design.

136 Diaphragm, convex design: Usually between 2.0" and 12.0" in diameter and a thickness ranging between 0.01" and 0.25". Can be made of various materials, including metals, carbon fiber, composites, or woods.

137 Diaphragm chassis, convex design: Usually between 2.0" to 12.0" in diameter and between 0.125" and 0.625" in thickness. Can be made of various materials, including metals, carbon fiber, composites, or woods.

138 Diaphragm sound chassis mount, convex design: Usually between 0.5" and 3.0" in diameter.

139 Diaphragm, outer wall, convex design.

140 Diaphragm cavity, inner wall, convex design.

141 Sound wave anti-reversion regulator: Usually varies in length between 0.125" to 2.0" and a diameter between 0.20" to 2.5". The material used is generally composite or wood.

142 Sound wave directional cone that is positioned within the passage of the anti-reversion regulator.

143 Sound wave anti-reversion regulator mount.

144 Sound wave solid regulator: Usually varies in length between 0.125" to 2.0" and a diameter between 0.20" to 2.5". The material used is generally composite or wood.

145 Sound wave regulator mount edge.

146 Sound wave pass through regulator: Usually varies in length between 0.125" to 2.0" and a diameter between 0.20" to 2.5".

147 Sound wave passage: Usually has a diameter between 0.20" to 2.5".

148 Sound chassis snap mount for all regulator types.

151 Expansion chamber: Usually has a diameter between 0.20" to 2.5" and a chamfer range between 20 and 65 degrees.

152 Sound wave regulator filter.

153 Sound wave regulator filter passage.

155 Exploded modular acoustic sound processor, convex design.

156 Assembled modular acoustic sound processor, convex design.

157 Sound chassis 122 and cover 113 assembled, top piece, convex design.

158 Sound chassis 123 and cover 114 assembled, bottom piece, convex design.

159 Sound chassis, front piece, ellipsoid design: Can be a hybrid of various materials, including metals, composites, plastics, or woods.

160 aperture in which the condenser microphone can protrude into the ellipsoid sound processor chamber.

161 Side adjustable external sound collector/deflector, ellipsoid design.

162 Lower adjustable external sound collector/deflector, ellipsoid design.

163 Sound chassis, rear piece, inner cavity, ellipsoid design.

164 Sound chassis, rear piece, ellipsoid design: Can be a hybrid of various materials, including metals, carbon fiber, composite, or woods.

165 Generic condenser microphone, assembled.

166 Exploded modular acoustic sound processor, ellipsoid design.

167 Acoustic transmission line.

168 Virtual resonance chamber.

169 Resonance chamber baffles.

Figure 11:
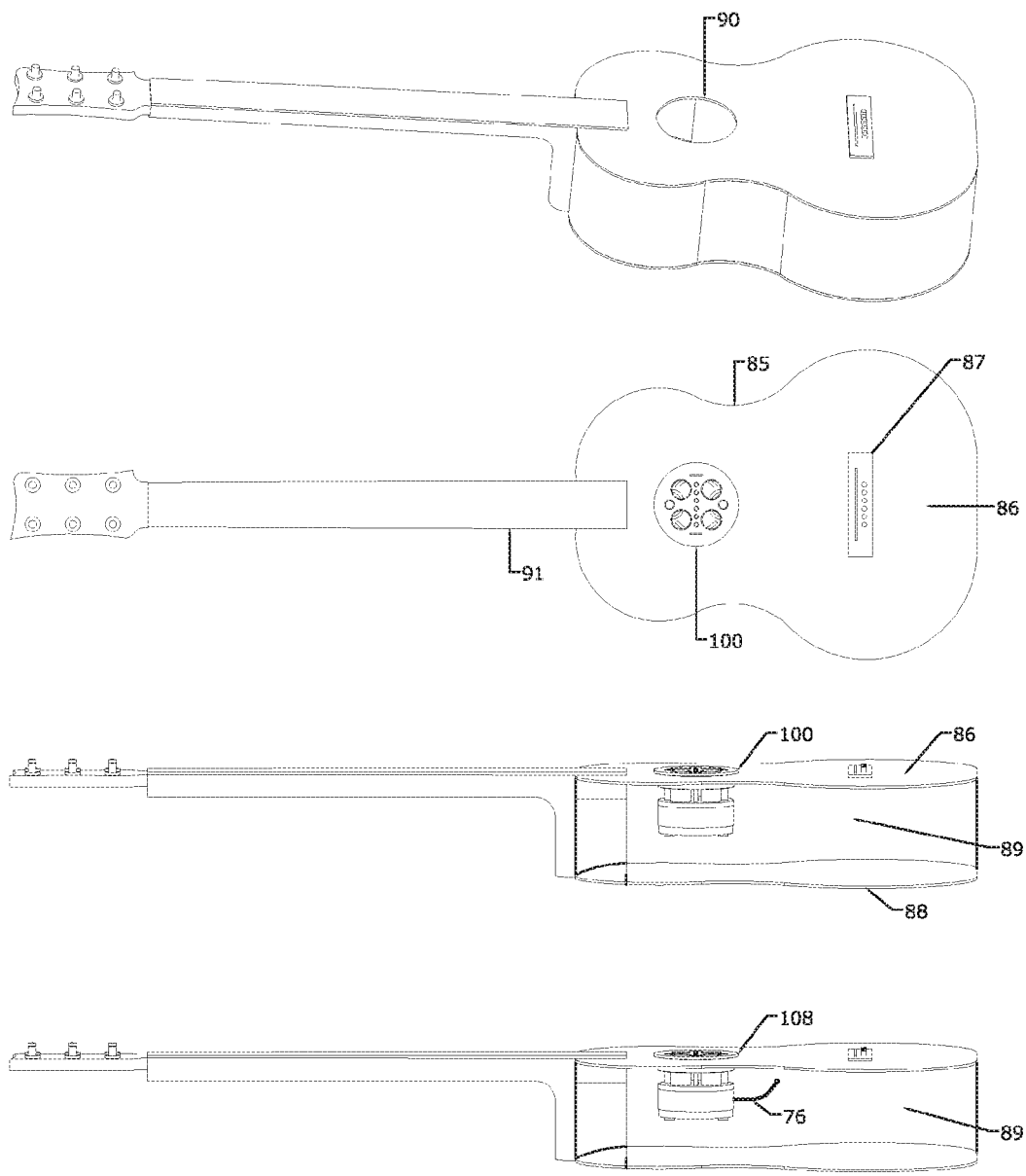
FIG. 11 is a front view and x-ray view of an acoustic instrument with and without the present invention in use, linear design application.

Referring to the acoustic guitar of FIG. 11, its strings are strung along its neck 91, over the sound hole 90, and connect at the bridge 87. When a string is struck, the strings vibrate the bridge 87 and ultimately the sound board top 86 and bottom 88, generating sound waves within the resonance chamber 89 of the guitar. Additionally, soundwaves generated directly from the strings themselves can pass through the sound hole 90 and into the resonance chamber 89 of the guitar. These sound waves pass out of the sound hole 90 of the guitar as the air pressure between the resonance chamber 89 and exterior of the guitar fluctuate with each sound wave.

Hence, an acoustic guitar may generate some sound directly emanating from the guitar strings, but much of the sound waves are a result of the strings conveying vibrations into the remaining portions of the guitar. In this regard, the sound hole 90 allows the exchange of air so that the body of the guitar can vibrate, while also allowing further sound waves to escape.

In one embodiment of the present invention (shown in two different perspective views in FIG. 1), an acoustic sound processor 100 for an acoustic instrument, such as the guitar of FIG. 11, is presented. Generally, the acoustic sound processor 100 is a multi-chambered device that is located at least partially within the sound hole 90 and resonance chamber 89 of the instrument, thereby limiting or adjusting both the sound waves and the air pressure changes into and out of the resonance chamber 89 of the instrument. The sound processor 100 can include multiple tubes or passages through its body that can allow for passage of the sound waves into different interior chambers of the processor, as well as other passages that completely bypass the chambers of the processor. In this manner, a combination of modified and unmodified sound can be created and pass into and out of the instruments interior.

In one embodiment, the acoustic sound processor 100 includes a top enclosure or sound chassis 1 that is sized to sit at or above the sound hole 90, a lower enclosure or diaphragm 69 positioned so that it is located within the instruments resonance chamber 89, and an inner enclosure or internal sound collector inner wall 48 that forms an internal sound collector chamber 47 between the inner wall 48 and the diaphragm 69. The sound collector chamber 47 can have a plurality of tubes 12*a* and 32*a* of different diameters that connect it to and are in communication with the exterior of the instrument, via apertures in the sound chassis 1. Further, additional tubes 22*a* can bypass the sound chamber 47 and the diaphragm 69, directly connecting the exterior of the guitar to the resonance chamber 90 by extending through the chassis 1, chamber 47, and diaphragm 71. In this respect, the sound processor 100 can allow some soundwaves to pass directly through, while blocking or modifying others. Additionally, other components can be optionally added to the sound processor, such as a rotary vibrato chassis 51, which is also illustrated in FIG. 1. The individual components of the sound processor 100 are described in further detail below.

FIG. 1 illustrates an exploded view of the modular acoustic sound processor 100 that demonstrates the modular, adjustable nature of the embodiment. For example, the modular acoustic sound processor 100 can be used with or without a sound collector 42 and/or with or without a diaphragm 69. In addition, varying diaphragm 71 materials, such as wood or carbon fiber, and varying materials for the tubes 12*a*, 22*a* 32*a*, such as brass or stainless steel, can be used to inject desired tone qualities into the sound waves. A further example of the adjustable nature of the design is that the diaphragm 69 can be placed closer or further away from the internal sound collector 42 and/or the sound chassis 1 to control resonance and air pressure to a greater or lesser degree.

Figure 3:
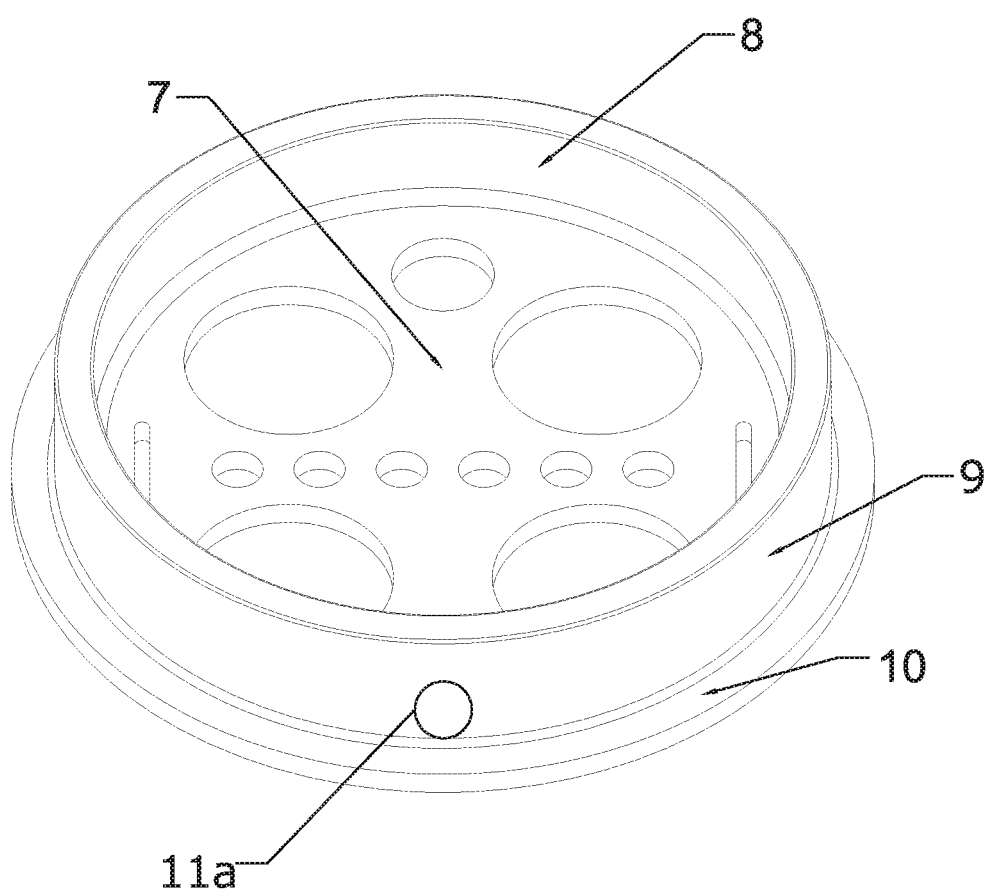
FIG. 3 is a bottom view of the sound chassis, linear design.

FIGS. 2 and 3 illustrate a top and bottom view of the sound chassis in which the sound waves flow in and out at different frequencies, velocity and decibel levels. The top sound board 2 connects to or allows exterior communication with the various modular units to the sound chassis 1. The balancing ports 3*a* vary in shape and size, depending on the type of acoustic instrument and model of the sound chassis 1, but are shown as being relatively rectangular in this embodiment. Unlike the other ports, these do not have any further tubes beneath them, allowing air or pressure communication between the exterior of the sound processor and the area formed between the interior side of the chassis 1 and the sound collector 42 (i.e., the sound chassis cavity 7). Since portions of the sides of the sound processor 100 are open (e.g., to the resonance chamber 89 of the instrument), the ports 3*a* balance the sound waves between the modular acoustic sound processor 100 and the instrument's resonance chamber 89.

The sound tube mounts 4*a* are apertures in the sound chassis 1 to the sound board 2 and hold the sound tubes 32*a* or the sound tube variations 35, 38 in place (referenced in FIG. 6). The sound chassis 1 blocks and deflects ambient noise from entering back into the instrument, reducing the regeneration of sound that causes feedback. It uses the bypass tubes 22 (installed in the bypass tube mounts 5*a*), sound tubes 32 (installed in the sound tube mounts 4*a*), inline tubes 12 (installed in the inline tube mounts 6*a*) and balancing ports 3*a* as part of the acoustic soundwave intake and output systems.

In FIG. 3, the chassis outer wall 9 reflects sound waves around the instrument sound board 86 (referenced in FIG. 11) downward to the resonance chamber 89 of the instrument to keep the sound waves from bottlenecking just underneath the sound board 86. This allows the instrument sound board 86 to vibrate freely. The sound chassis 1 and sound chassis cavity 7 collect sound waves and reflections from an external sound source and/or the instrument resonance chamber 89 of an instrument and transfers the sound into the internal areas of the modular sound processor 100. The sound chassis cavity inner wall 8 extends in a circular shape near the edge of the sound chassis cavity 7 and helps prevent outside noise from entering the instrument. The sound chassis support edge 10 seals the airflow between the sound chassis 1 and the instrument sound hole 90 and prevents leakage. The support edge 10 also keeps the sound chassis 1 aligned with the instrument sound hole 90. The sound chassis mounts 11*a* attach to the sound hole 90 with three to four small grommets 11*a*, securing the modular acoustic sound processor 100 to the instrument sound hole 90, eliminating the use of tools for installation.

The sound chassis 1 holds the inline tubes 12*a* (and/or the variations 15, 18) in place with an inline tube mount 6*a* (e.g., apertures in the sound chassis sound board 2) such that the inline tubes 12*a* connect the exterior of the sound processor 100 with the sound collector 42. The inline tube mounts 6*a* generally extend linearly along the sound chassis sound board 2 and are preferably spaced so as to be each located under one of the strings of the instrument (e.g., each mount 6*a* is located under one of six guitar strings), which allows the tubes 12*a* to import sound from each of the individual instrument strings. Each tube 12*a* can further have a round, square, rectangular, or other shaped diameter. The inline tube 12*a* can sit flush with the sound chassis 1 or may protrude outward from the board 2. Varying compression and equalization can be created by substituting one or more of the inline tubes 12*a* with a tube variation 15, 18 (also seen in FIG. 4).

The inline tube 15 (referenced in FIG. 4) is generally similar to the inline tube 12*a* (a cylindrical tube) with the addition of an angle cut 17 at one or both ends. This cut 17 may vary in degrees—perpendicular or compound—to the tube surface. The angle cut 17 changes the sound wave shape, pressure levels, and wave lengths allowed into the tube at either end by increasing or decreasing the amount of space able to enter 13 and/or exit 14, 17.

Figure 4:
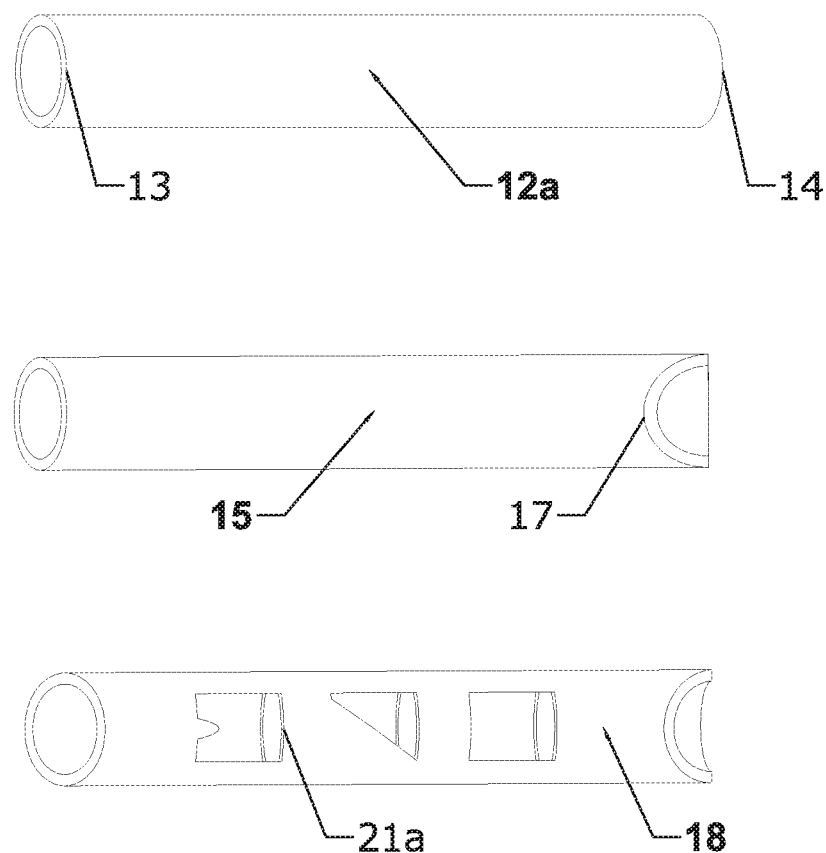
FIG. 4 is a side view of the inline tube variations.

A further variation is illustrated in FIG. 4, illustrates three side ports 21a on the tube 18. The side port 21a openings are perpendicular to the curved side surface of the inline tube 18. The shape and number of the ports 21a can vary and the location center line vector points can be asymmetrical to each other. When the sound processor 100 is assembled, the ports 21a are positioned between the chassis 1 and the sound collector 42, as well as between the sound collector 42 and the diaphragm 69. Since the areas that these ports 21a are located do not have sidewalls or other blockages on the sound processor 100, the ports 21a are in communication with the resonance chamber 89 of the instrument. The ports 21a allow the instrument's first generation sound wave to separate, which allows the sound wave to pass directly to the resonance chamber 89 of the instrument and also to the remaining systems of the processor 100. This, when implemented, causes a short delay of the sound wave, approximately between 0.01 to six milliseconds, to reach the end point 14, 17 of the tube 18 or the sound collector 42. This delay adds a thickening effect of the instrument's overall sound to specific summing junctions while helping to reduce regenerated sound that causes feedback. Collectively, the ports 21a equalize the passing tones of the resonance chamber 89 by adding or cutting the frequency amplitude of the sound waves from the instrument. The degree to which the sound wave is processed depends on the shape, size and material of the inline tubes 12a, 15, 18 and the shape, size and number of ports 21a or the absence of ports.

The sound chassis 1 also holds the bypass tubes 22a or the variations 25, 28 in FIG. 5 in place with bypass tube mounts 5a. The bypass tubes 22a are positioned such that the open end 23 is located at the chassis 1 and the opposite open end 24 is located at opening 67a of the diaphragm 69, such that the body of the bypass tubes 22a passes through ports 43a and 52/53. In this respect, the sound waves from the resonance chamber 89 of the instrument bypass the sound collector 42, rotary vibrato chassis 51, and diaphragm 69 and thereby allow passage of part of the unaltered sound waves to the top 86 and bottom 88 sound boards of the instrument (FIG. 11), as well as allowing airflow to move freely into and out of the resonance chamber 89. The bypass tubes 22a, 25, 28 also act as a structural support for the placement and rigidity of the components of the sound processor 100.

As seen in FIG. 5, the bypass tube 22a can be a straight tube and can possess any diameter shape such as round, square, rectangular, or a custom shape. The alternate design of bypass tube 25 is generally similar as the bypass tube 22a with the addition of an angle cut 27 at one or both ends. This cut 27 may vary in degrees—perpendicular or compound—to the tube surface. The angle cut 27 alters the soundwave pressure levels and wave lengths allowed into the tube by increasing or decreasing the amount of space to enter 23 and or exit 24, 27, depending on whether the cut is facing inward or outward. Alternate bypass tube 28 is also similar to the previously described tubes 22a and 25, but further includes ports 31a that are perpendicular to the curved side surface of the bypass tube 28, allowing soundwaves to enter and exit into the resonance chamber 89 of the instrument. These ports 31a align between either the sound collector 42 and chassis 1, or between the sound collector 42 and the diaphragm 69. Since those areas lack sidewalls or other blockages on the sound processor 100, the ports 31a are in communication with the resonance chamber 89 of the instrument. The shapes of port 31a may vary, such as rectangular and triangular, and the location center line vector points are not always symmetrical to each other (i.e., the ports 31a may not necessarily be aligned along the tube's length). The ports 31a allow the tail end of the vibrations and reflections from the instrument resonance chamber 89 to blend into the unaltered signal coming from the bypass tubes 28. The ports 31a also add equalization to the resonance chamber 89 by adding or cutting the frequency of the sound wave amplitude received from the source frequencies. The degree to which the sound wave is processed depends on the shape, size and material of the bypass tubes 22a, 25, 28 and the shape, size and number of ports 31a or the absence of ports.

Sound tubes 32a (illustrated in FIG. 6) are used to process input and output levels of the sound waves and allow air pressure levels to flow in both directions. More specifically, they are positioned to capture a broader spectrum of the sound source, rather than a specific sound focal point, as in the inline tubes 12a. The sound tube 32a can sit flush with the sound chassis 1 and protrude inward into the internal sound collector 46. They also may protrude outward from the sound chassis 1, depending on the instrument configuration. This is beneficial, as it can phase cancel the regenerated sound coming from outside sources by adjusting the sound waves out of time and changing the shape, while reversing the regenerated sound wave out of the processor, blocking and deflecting it from entering back into the resonance chamber 89, while maintaining a suitable airflow rate. This self-timing system offsets the relationship of both the primary (natural) sound source and the processed sound source, keeping them from overlapping and causing signal interference.

The sound tubes 32a are designed in length and diameter to act as an equalizer, modifying the acoustic instrument sound spectrum. This is generally performed by ear, to the taste of the person performing the modification. The material used in the sound tubes 32a injects the characteristics of the type of material into the sound waves and then reflects the injected sound waves back into the resonance chamber, in combination with the natural qualities of the sound source. The sound tubes 32a also act as a built-in mechanical dynamic compressor by capping loud sound pressure levels and keeping quieter sound pressure levels unaffected.

FIG. 6 also illustrates several alternate embodiments of sound tube 32a. For example, sound tube 35 is generally similar as the sound tube 32a with the addition of an angled or curved cut 37 at one or both ends. This cut 37 may vary in degrees—perpendicular or compound—to the tube surface. The angle cut 37 allows larger wave lengths into the tube by increasing the amount of space to enter 33 and or exit 34, 37. Sound tube 38 is another embodiment that is generally similar to the tubes 32a and 35, but further includes ports 41a located along the curved side of the tube and open into the tube's interior. The port shapes 41a may vary, such as rectangular or triangular, and may be either aligned or misaligned down the tube's length, and either symmetrically or asymmetrically positioned relative to each open end of the tube. The ports 41a transfer the sound wave into and out of the processor assembly 100 at different velocity and speed rates, depending on the size and shape.

The sound waves released from the sound tube ports 41a changes the reflective degree of the sound wave and sound pressure, directing them to project and reflect in the resonance chamber 89 to energize the diaphragm 65. In this embodiment, the ports 41a receive sound waves from the vibration of the strings, resonance chamber 89 and sound board of the instrument 86 to be processed within the sound processor system 100. The degree to which the sound wave is processed depends on the shape, length, diameter and material of the sound tubes 32a, 35, 38 and the shape, size and number of ports 41a or the absence of ports.

The tubes referenced in FIGS. 4, 5 and 6 can transport sound straight into the resonance chamber 89 or accumulate it in the internal sound collector 42, depending on the configuration of the modular system. The internal sound collector 42 illustrated in FIG. 7 shows bypass tube mounts 43a, inline tube mounts 44a and sound tube mounts 45a to accommodate bypass tubes 22a, inline tubes 12a and sound tubes 32a; however, the internal sound collector 42 may or may not have all tube types represented on all models. Each internal sound collector 42 preferably includes a bottom seal 49, an inner wall 48 and an outer wall 46 to isolate processed sound waves in the cavity 47 and keep them separate from the resonance chamber 89 sound waves. This internal collector acts as a summation junction.

Figure 9:
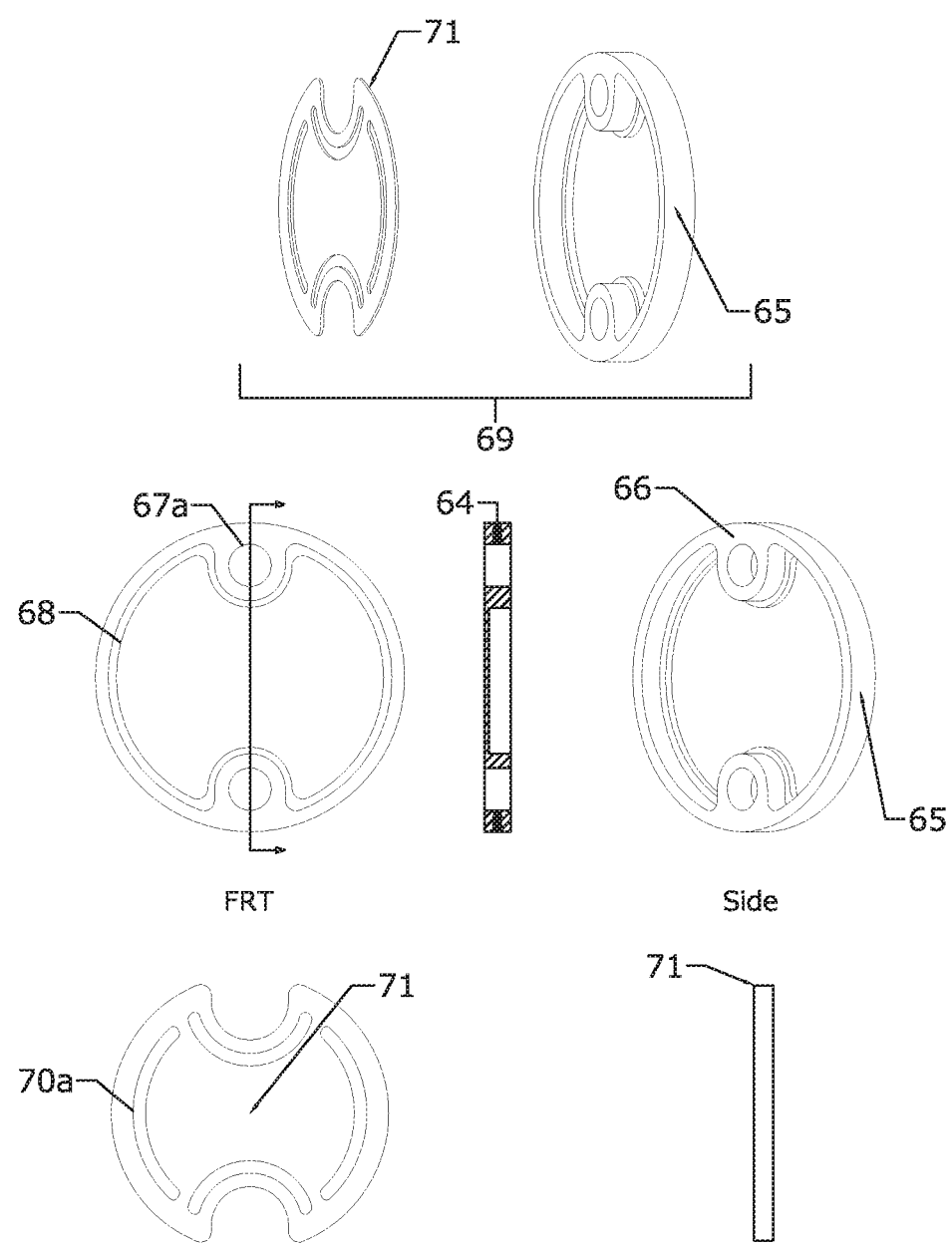
FIG. 9 is front and side views of the diaphragm chassis and diaphragm, both linear design.

The diaphragm chassis 65 preferably includes a mount edge 68 for mounting the diaphragm 71, at least two bypass tube mounts 67a, and a surface seal 66 (referenced in FIG. 9). The diaphragm 71 can be made of a material that is different from the chassis 65 (such as carbon fiber or aluminum) and it can be solid or have slots 70a. Alternatively, the diaphragm 71 can be constructed out of the same material as the chassis and built as one solid unit 69. When the diaphragm assembly 69 is constructed of two pieces, the diaphragm 71 is press fit or glued into the mount edge 68 of the chassis 65. Generally, the diaphragm assembly 69 is placed behind the sound collector 42 (i.e., further into the resonance chamber of the instrument) and is either spaced to release air pressure between the two pieces or closed by way of the collector bottom seal 49 and diaphragm surface seal 66. However, the diaphragm 69 can also be used effectively in the sound processor 100 without the sound collector 42. The diaphragm 69 is held in place by set screws 20, which are secured to the bypass tubes 22a. In addition to spacing and securing the diaphragm assembly 69 and the sound collector 42, the set screws 20 are used to hold in place all modular pieces, using the bypass tubes 22a as an anchor.

The diaphragm assembly 69 (referenced in FIGS. 1 and 9) can serve multiple purposes. One purpose is to inject the characteristics of the diaphragm material and shape/modify the sound waves, changing the harmonic series. It may also change the sound pulse sensitivity, the equalization, and compression stature. This changes the overall sound wave output of the associated instrument, allowing the instrument to morph sound textures. Another purpose is to project sound wave pules to a designated area of the resonance chamber altering the signal pathways.

Since the diaphragm assembly 69, sound collector chassis 42, and vibrato assembly 55 are all fixed on bypass tubes 22a, they can be linearly moved relative to each other to further modify the sound created by the sound processor 100.

Figure 14:
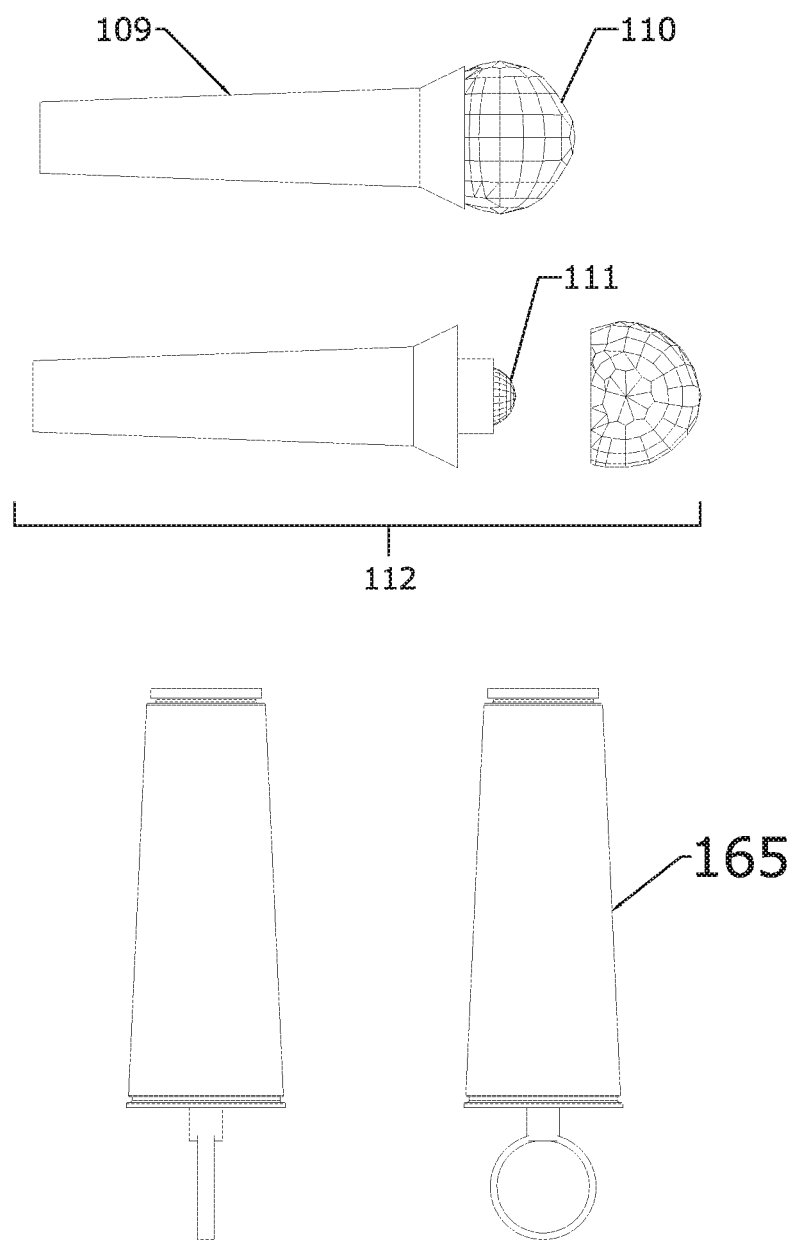
FIG. 14 is a side view of a dynamic and condenser microphone without the present invention in use.
Figure 15:
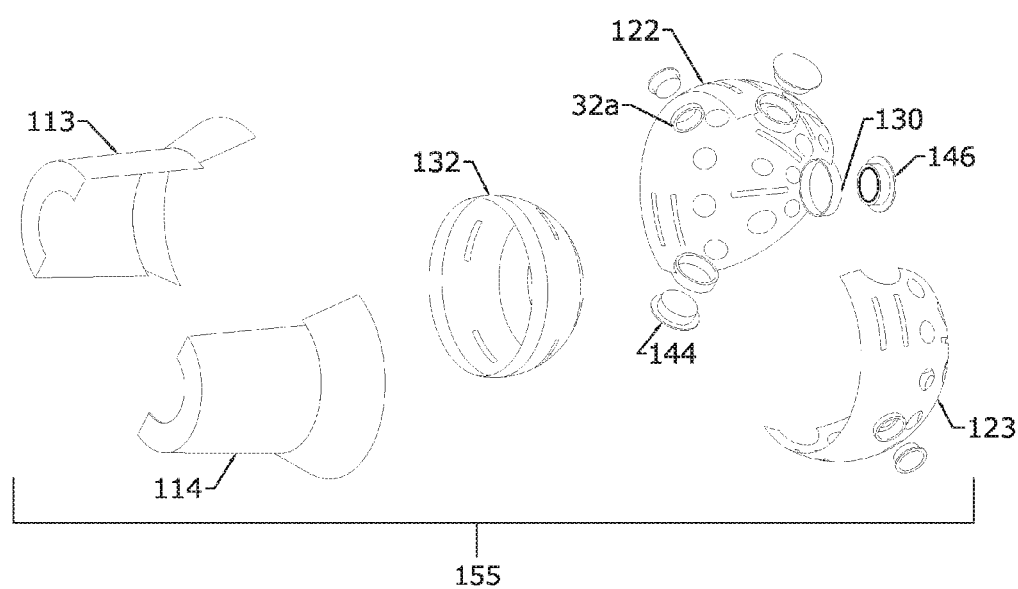
FIG. 15 is an exploded perspective view, showing the modular and adjustable parts of the present invention, convex design.
Figure 16:
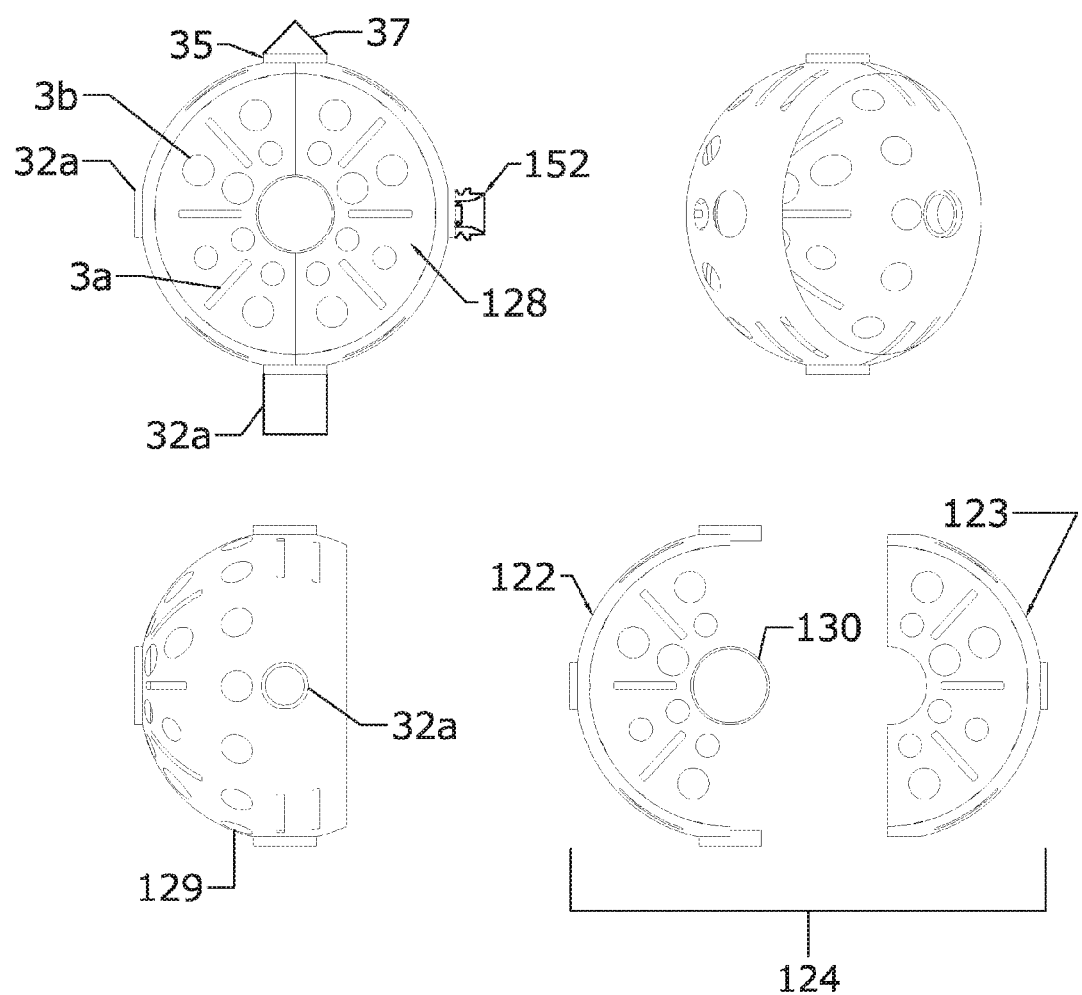
FIG. 16 includes a top, isometric, side and exploded view of the top chassis of the present invention, convex design.
Figure 17:
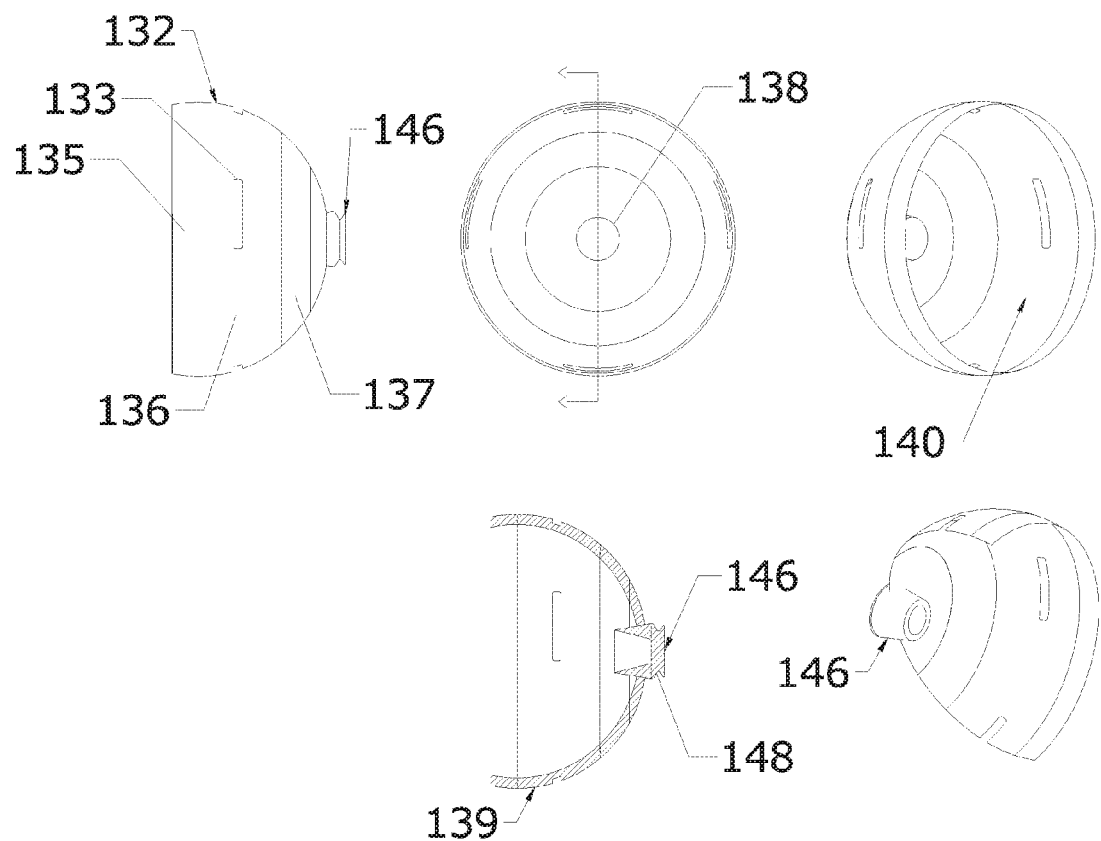
FIG. 17 includes a side, top, isometric, cross hatch side and cross hatch isometric view of a diaphragm and pass through mount, convex design.
Figure 18:
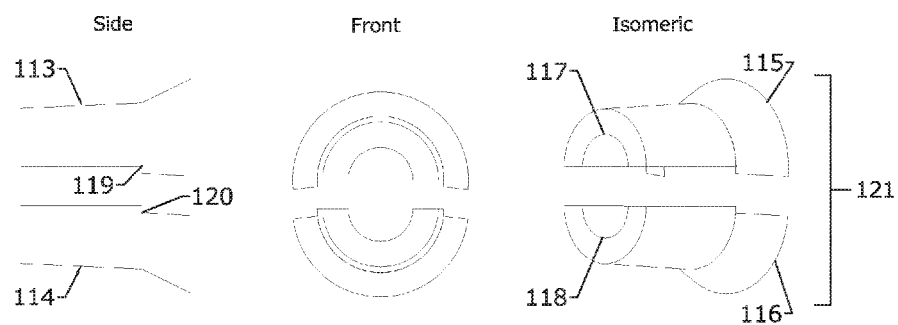
FIG. 18 includes a side, top and isometric view of the sound chassis mount, convex design.
Figure 27:
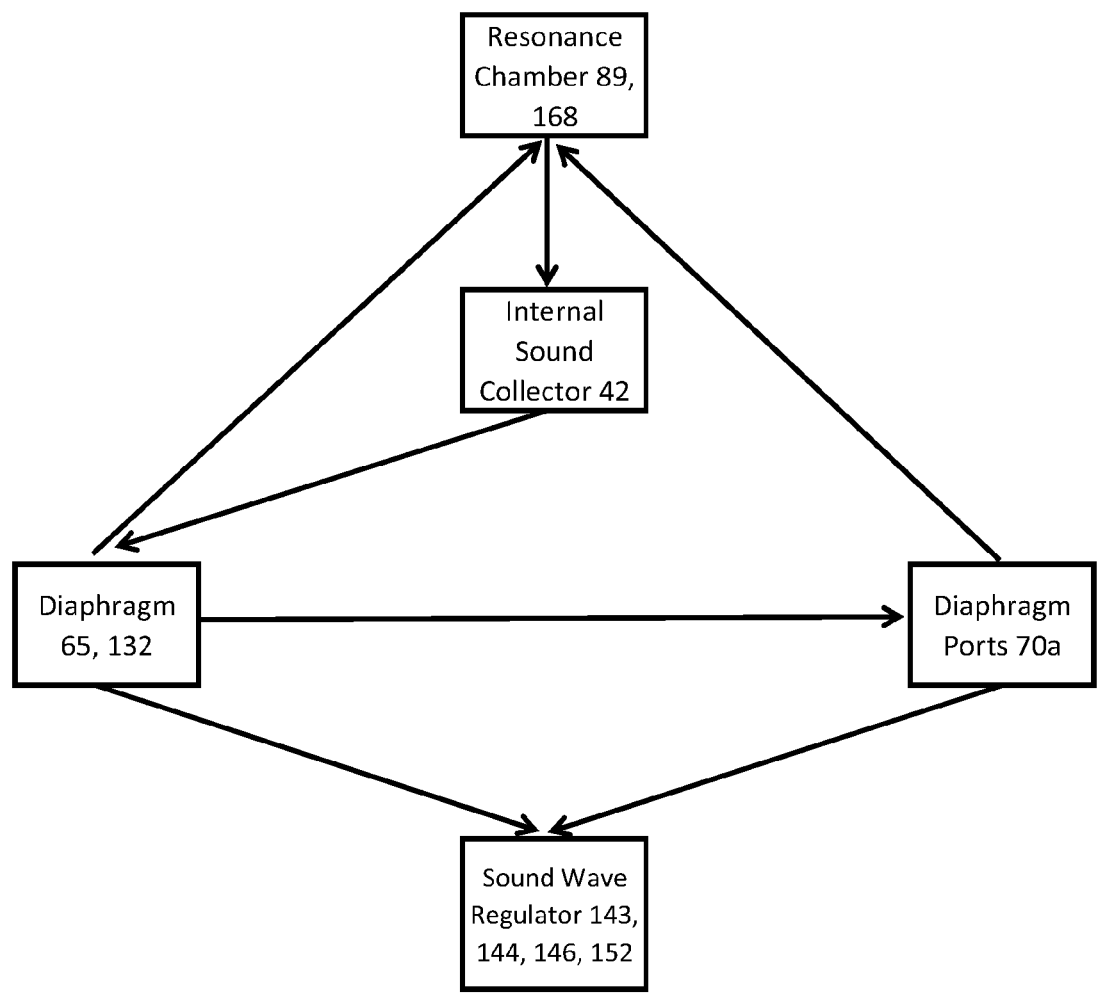
FIG. 27 is an acoustic soundwave resonance control system pathway.

Other embodiments of the present invention allow sound processors to be added to or built with their own resonance chambers and sound processors. For example, the convex sound processor 156 (FIGS. 15-22) can be used with a dynamic microphone as illustrated in FIG. 14, and/or a piezo pickup. The ellipsoid sound processor's 166 (FIGS. 23 and 24) design applications include transducers, such as a dynamic microphone 109 as illustrated in FIG. 14, a condenser microphone 165, a piezo pickup, or with an acoustic transmission line 167 (FIG. 27). These embodiments differ from the linear design of sound processor 100 in that they create their own resonance chamber that was not originally part of the microphones or piezo pickups, rather than fitting within an existing resonance chamber (e.g., chamber 89 of a guitar). The resonance chamber allows the interconnected set of tubes and chambers of the acoustic sound processor to work properly, thereby creating an enclosure in which sound waves can be manipulated and multi-processed.

Figure 21:
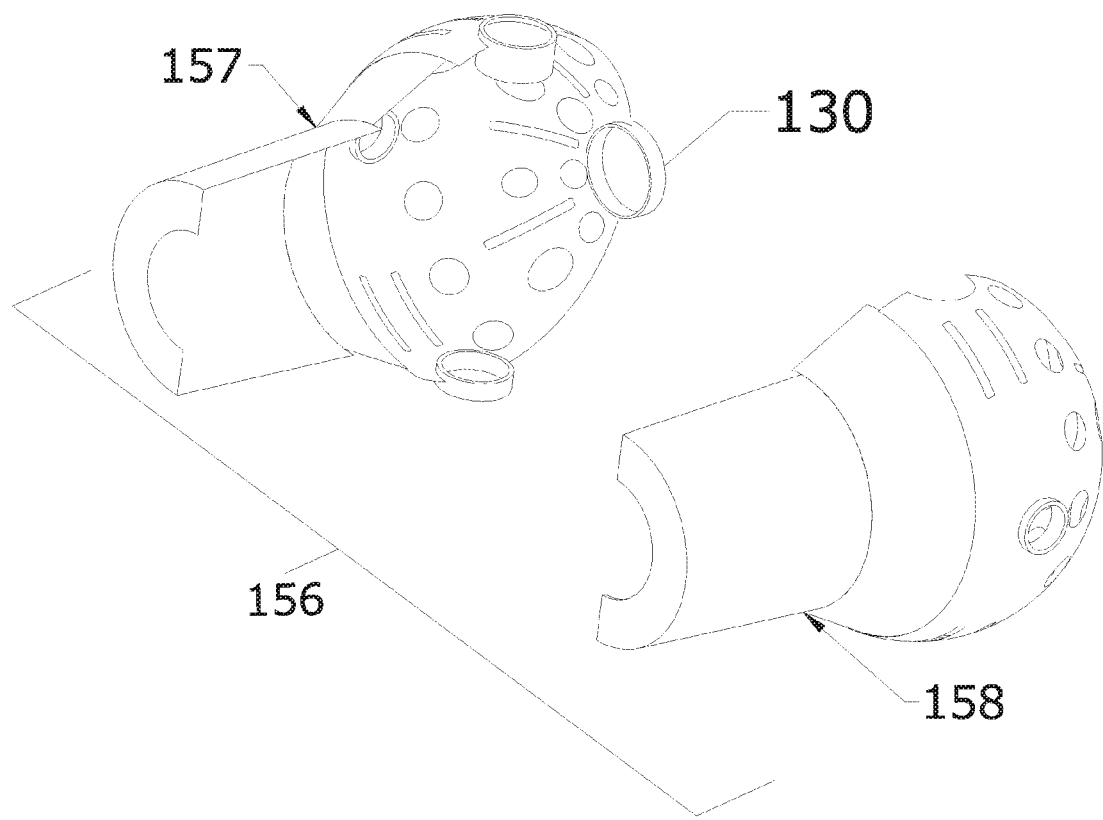
FIG. 21 is a perspective view of the assembled top and bottom pieces of the present invention, convex design.
Figure 22:
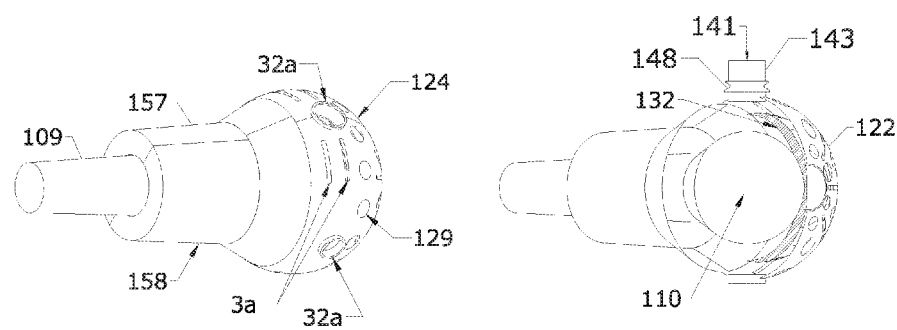
FIG. 22 includes x-ray and perspective views of a dynamic microphone with the present invention in use, convex design.
Figure 23:
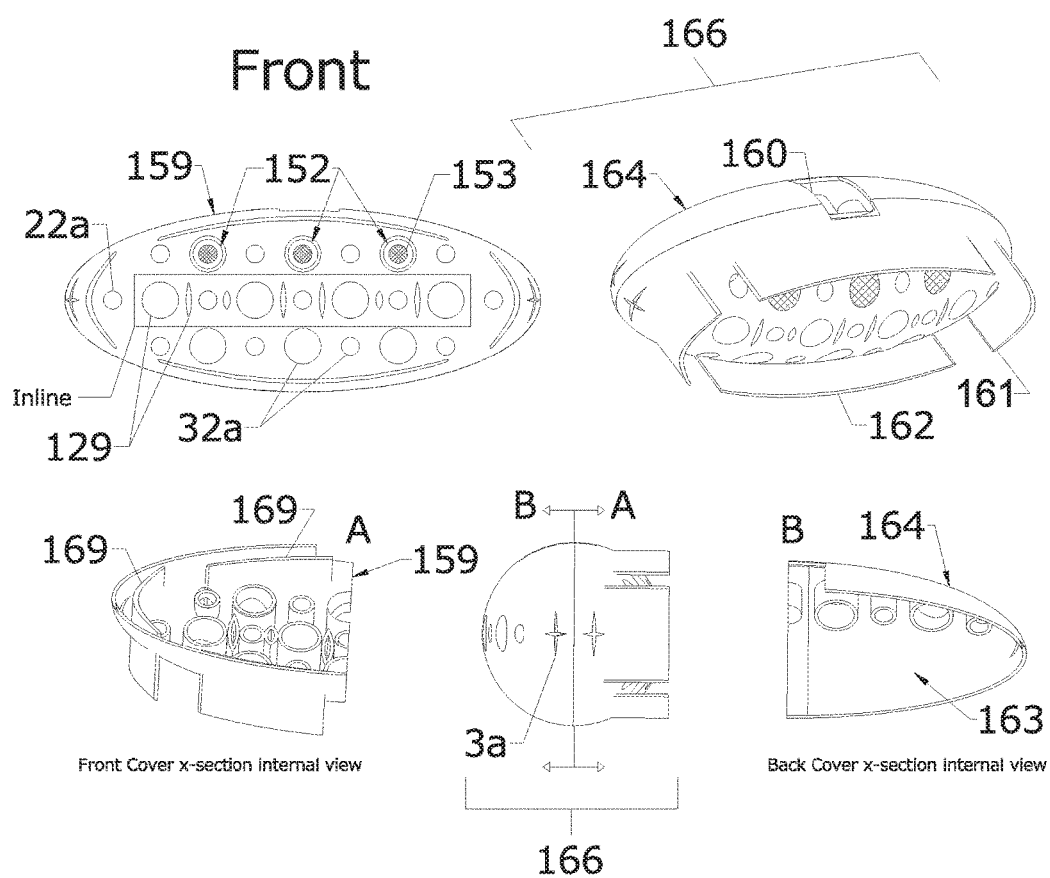
FIG. 23 is a front, perspective, cross hatch and side views of the assembled present invention, ellipsoid design.

FIGS. 15-22 illustrate various views and components of the convex sound processor 156 for a standard dynamic microphone 109 (shown in FIG. 14). The processor 156 is comprised of lower cover components 113, 114 and sound chassis components 122, 123 that are joined together in the manufacturing process to makeup the outer housing of the processor 156 (FIG. 21). These two pieces 157, 158 are snap locked around a transducer for installation. In FIG. 22, this assembly 156 of pieces 157 and 158 is shown with a dynamic microphone 109 as one potential application.

The convex top sound chassis 124 (assembled of components 122, 123) functions similar to the sound chassis 1 of the linear sound processor 100. However, the dome shape of the convex chassis 124 facilitates omni-directional sound importing and processing. Similarly, the diaphragm 132 of the convex sound processor 156 functions similar to the diaphragm 69 in the linear processor 100, but allows omni-directional sound transporting and processing.

The ellipsoid and convex sound processors create the capability to have one or more separate focal points within one or more axes in a single processor. This is also true for the sound tubes 32a. The sound tubes 32a can intake one or more broad areas of the sound waves, which can then be split up and down, front and back and/or side to side, so as to be directed through the sound regulators 143, 144, 146 and/or 152 and/or the collector/deflector 161 and 162 (explained later in this specification), which allow for sound processing. With the use of the sound regulators 143, 144, 146 and/or 152, the ratio of the focused intake from the inline ports 13 to the broad intake from the sound ports 33 can be regulated within the resonance chamber 89, 168. By varying the ratio, the mix can be customized for each axis.

Figure 24:
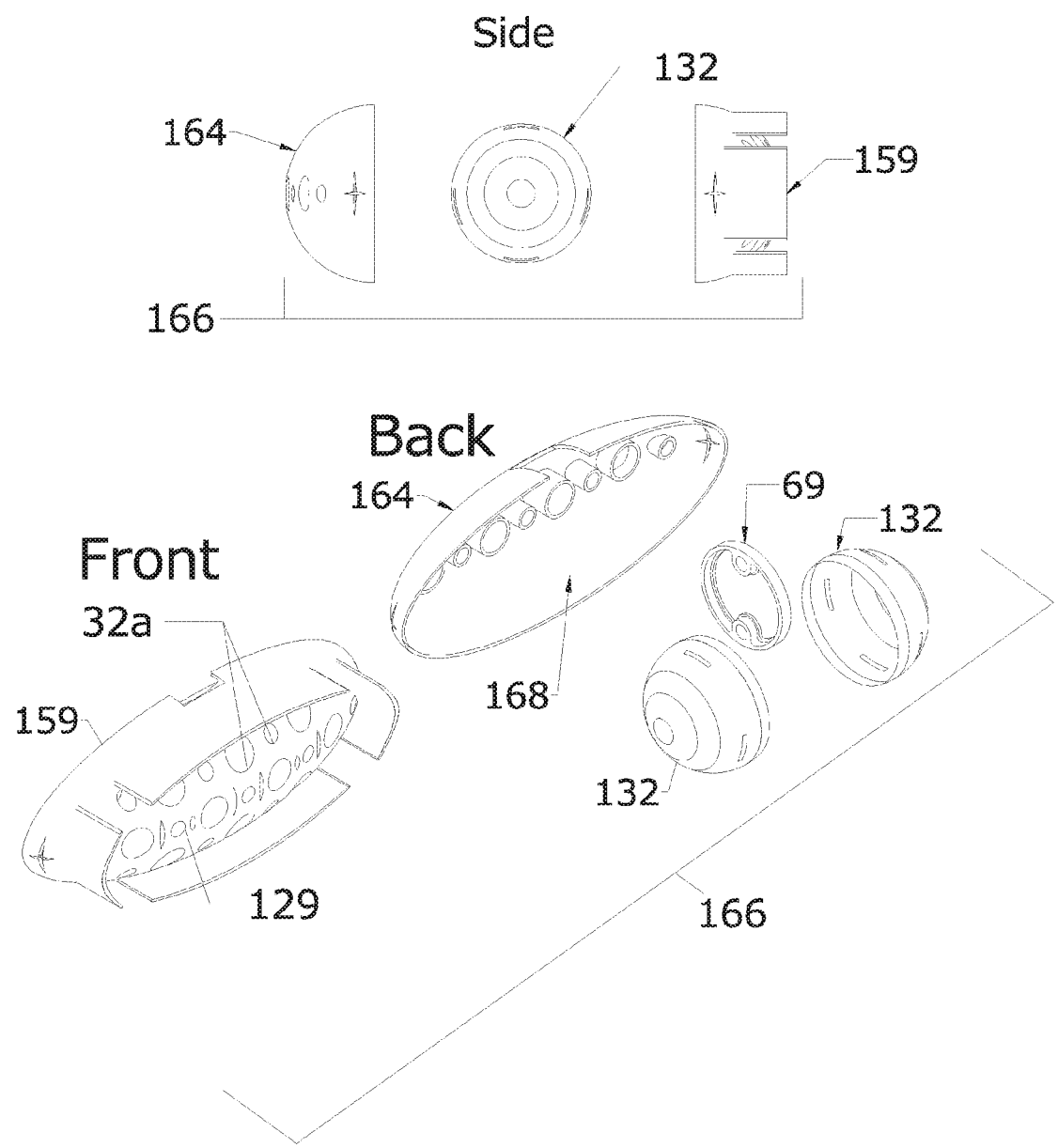
FIG. 24 includes a side and isometric exploded view of the present invention, ellipsoid design.

In FIG. 24, the ellipsoid acoustic sound processor 166 may include a flat diaphragm 69, a convex diaphragm 132, or both, which create a variety of options for manipulating or enhancing the sound waves, depending on the mix of materials, design, types and placement of the diaphragms 69, 132. When a diaphragm is a convex design 132, the facing direction of the apex within the processor 166 gives a further modification option. These diaphragms 69, 132 reside within the assembled ellipsoid sound processor 166. The front and rear sound chassis pieces 159, 164 have pockets that allow the diaphragm 69, 132 to be placed in position by the sound chassis snap mount 148.

Using different diaphragm materials for each of the diaphragms 69, 132 can combine, alter tones, equalize and manipulate the attack and release rate of compression separately. Using carbon fiber for one diaphragm will create fast attack and fast release, while using wood for the second diaphragm will create a slower attack and slower release. Equalization is achieved by reflecting the different materials into the resonance chamber 168. For example, carbon fiber can brighten the sound waves while maple wood can focus on the low to mid-range of the equalization spectrum. The compression threshold can be adjusted with placement of each of the diaphragms 69, 132 in proximity to the sound chassis 166 to allow separate input and output compression.

The shape of the diaphragm 69, 132 can be altered to manipulate the sound waves, as well. One example is using a convex diaphragm 132 and a linear diaphragm 69 in the same processor. The convex diaphragm 132 with the apex facing outward toward the exterior of the sound chassis 166 will allow more bass because of the low frequency sound wave's natural ability to bend, and disperse the high frequencies around the convex diaphragm 132 as the sound waves enter into the resonance chamber 168. The linear diaphragm 69 facing parallel to the body of the sound chassis 166 will deflect the high frequencies outward into the atmosphere or project them inward into the resonance chamber 168, depending on the type of diaphragm (i.e., slotted, solid, etc.) employed and the proximity to the sound chassis 166. If the convex diaphragm 132 is used with the apex facing inward toward the center of the resonance chamber 168, it will act as a bass trap, minimizing the bass that enters into the resonance chamber 168, while projecting and amplifying the higher frequencies, depending on the type of diaphragm (i.e., slotted, solid, etc.) and materials used.

As described further below, the convex sound processor 156 and the ellipsoid sound processor 166 may contain a pass through sound regulator 146, a solid sound regulator 144, a sound wave anti-reversion regulator 141, and a sound wave regulator filter 152. These regulators can help determine the direction of sound waves that enter or exit the sound processor 156, 166.

Another feature illustrated in the ellipsoid sound processor 166 is the sound collector/deflector 161, 162. The collector/deflector 161/162 are walls extending around and adjacent to the ellipsoid area containing the sound tubes 32a on the sound chassis front piece 159. This allows the processor 166 to collect sound in a desired direction and import it into the inline tube 12a and sound tubes 32a, and deflect the unwanted sound wave source away from the input system. This type of sound collector does not affect the air pressure of the resonance chamber 168 because it does not contain sound regulators 143, 144, 146, 152 or sit inside of the resonance chamber 168 like the internal sound collector 42. The sound collector/deflectors 161, 162 can be telescoping and designed to slide easily in and out of the chassis front piece 159. Changing the depth of the collector 161, 162 will regulate the quantity of sound waves collected and deflected.

The sound regulators 143, 144, 146, 152 shown only in the convex sound processor are part of the acoustic soundwave resonance control, intake and output systems. Although only shown in the convex design, the sound regulators can be incorporated into all variations of the sound processors described or contemplated by the present specification. As best shown in FIG. 19, the sound wave regulator 146 has a pass through passage 147 which will function differently depending on the orientation or direction it is installed. When the tapered side is pointing outward from the processor, it will compress the input signal entering in the processor 156, 166. This differs from the regulator 144 because it compresses as it enters into the processor 156, 166 and the regulator 144 only compresses when the sound wave has already entered the processor 156, 166. When the regulator 146 is pointing inward toward the resonance chamber 168, in the opposite orientation as described above, it will expand the input signal into the processor 156, 166. In either case, regulator 146 will not affect the direction from which sound waves enter the processor 156, 166.

The sound wave regulator 146 helps to achieve a desired sound within the resonance chamber 168 and acoustic soundwave output systems. More specifically, the sound regulator 144 determines where the sound waves enter the processor 156, 166. For instance, if you install a sound regulator 144 on the back and sides of the processor 156, 166 the acoustic soundwave intake system will only process the sound waves from the front of the processor 156, 166. This allows the user to manipulate the direction from which the sound waves will be processed.

In another example, a sound regulator 146 or a similar tube can connect between the diaphragm 132 and the sound chassis 122, connecting an exterior of the processor 155 with the interior of the diaphragm 132, thereby bypassing the resonance chamber.

In another example sound regulators 144 are positioned on half the system tubes 12a, 22a, 32a on the back and sides of the sound processor 166. The front of the processor 166 will focus on the subject and allow sound waves from the remaining open tubes 12a, 22a, 32a to enter in the resonance chamber 168 and give the user control of the ratio of the combined incoming sound waves. In either example, using the sound regulators 144 changes the atmospheric pressure within the chamber 168 and gives the user the ability to control the amount of compression the sound waves will process. If the user would like to control the amount of compression without regard to direction, the sound regulators 144 would be placed in ports 13, 23, 33 on all sides of the processor 156, 166.

The sound wave anti-reversion regulator 141 (also shown in FIG. 19) is another variation of a sound regulator that allows sound waves to mostly enter in one direction. The regulator 141 can act similarly to sound regulator 146 but does not affect the amount of sound compression because it maintains the same sound pressure levels when pointing outward. When regulator 141 is pointing inward, it will act in a similar way as regulator 146 but will also be used to aide in the direction of the sound wave intake while controlling the output sound pressure levels.

Another variation of the sound wave regulator is the sound wave regulator filter 152. This is a mechanical device used to determine the input and output frequencies passing through the processor 156, 166. The physical structure of the filter 152 includes one or multiple perforated metal screens 153 placed within a tube with a funneled passage. This variation alters frequencies based on the diameter and pattern of the perforated holes. If more than one perforated metal screen is used, they can be layered and rotated to further allow or block select sound frequencies, as is known in those in the art.

Figure 8:
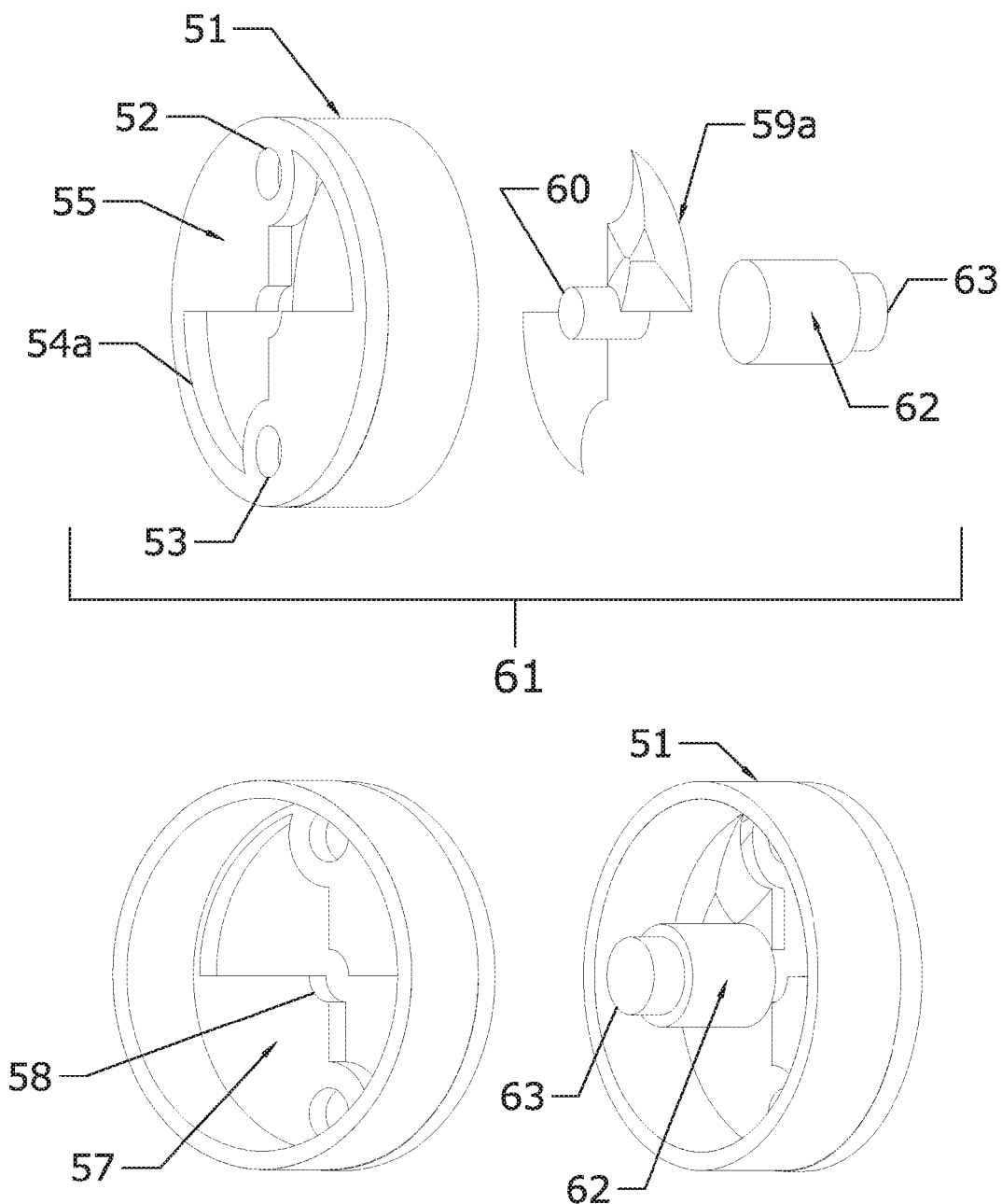
FIG. 8 is a perspective view of the rotary vibrato and complete assembly view, linear design.

An additional modular option, especially for the sound processor 100 as shown in FIG. 1, is the rotary vibrato assembly 61(shown in detail in FIG. 8). It consists of a rotary vibrato chassis housing 51, rotary motor 62, rotary motor shaft 60 and blade 59a. The accessory is powered by a small 1.3 volt battery 63. The airflow opening 54a allows sound to flow in and out of the chassis cavity 57, while the rotary top sound board 55 restricts airflow to the cavity 57. The motor 62 and the blade 59a are assembled into the shaft 60, which is press fit into the shaft mount 58 of the rotary vibrato chassis 51. The entire assembly 61 is secured to the processor 100 by the chassis bypass tube mounts 52 and the on/off switch opening 53. Used with the modular sound processor 100, the rotary assembly 61 becomes part of the resonance control system. The blades 59a rotate, systematically covering and uncovering the airflow opening 54a. This allows sound to enter the cavity 57 as an open and closed gate creating a chorale, tremolo and vibrato effect.

Figure 10:
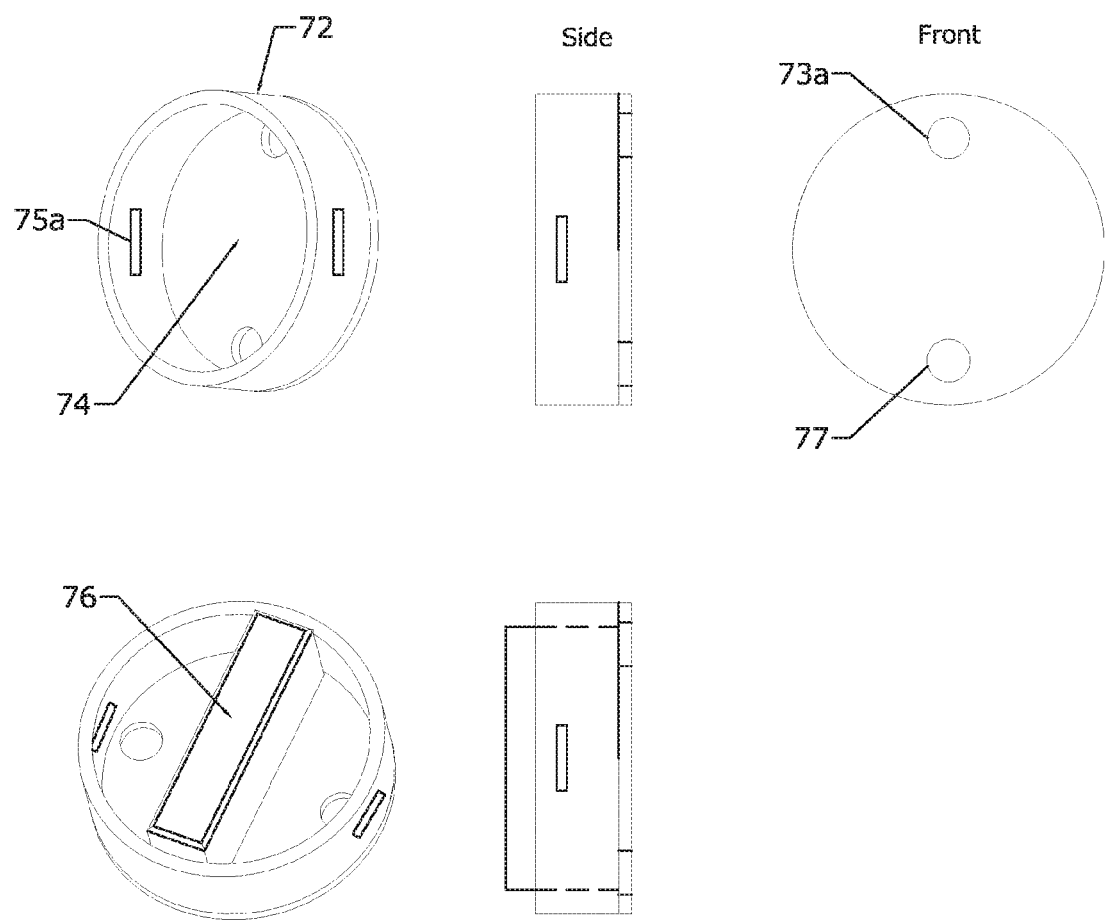
FIG. 10 is a perspective view of the wireless chassis holder, including top, side and bottom views, linear design.
Figure 12:
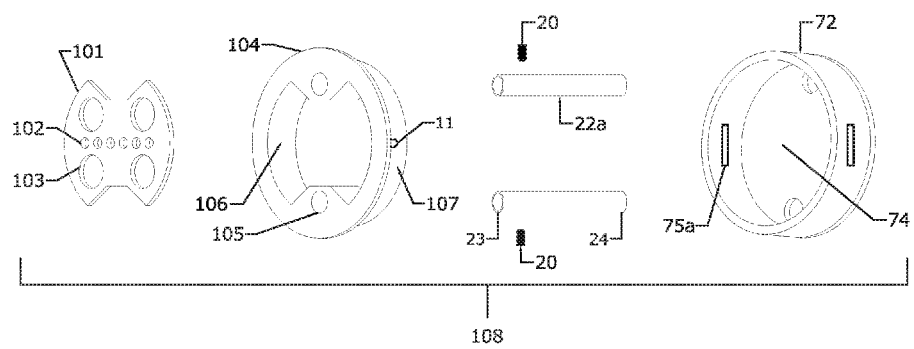
FIG. 12 is an exploded view of wireless chassis housing, top cover and bottom, linear design.
Figure 13:
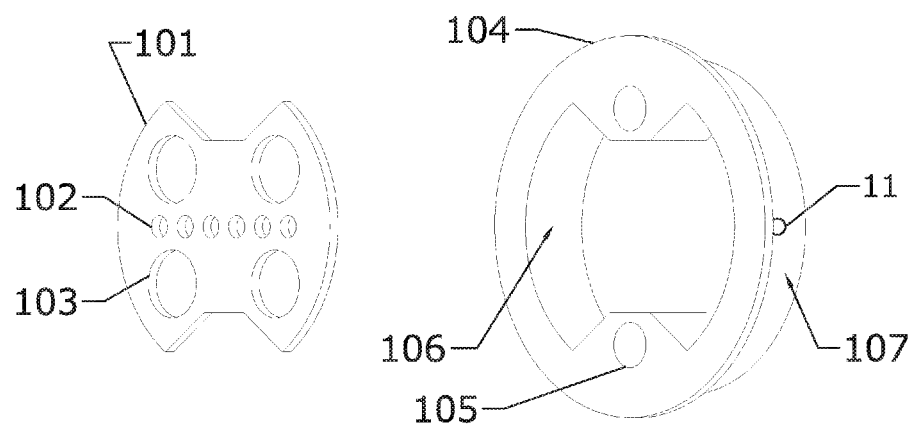
FIG. 13 is a front view of the top wireless chassis housing and cover, linear design.

A further modular optionis the wireless chassis holder 72 and wireless modular acoustic sound processor 108, as referenced in FIG. 10, FIG. 12 and FIG. 13 (though also applicable to sound processor 100 in a similar position to the vibrato in FIG. 1). The aftermarket wireless transmitter/preamp/microphone and or pickup 76 is held in the wireless chassis holder compartment 74 with Velcro straps that are fed through strap knockouts 75a. The wireless chassis holder 72 has bypass tube mounts 73a and an on/off switch opening 77 to secure the entire assembly to the modular acoustic sound processor 100. When fitted with an aftermarket wireless transmitter/preamp/microphone and/or pickup 76, the wireless chassis holder 72 allows the user to place an aftermarket transducer to a desired position within the output system to amplify the processed acoustic soundwaves into an electronic audio signal as part of the wireless modular acoustic sound processing system 108. This eliminates the necessity to separately modify the instrument to accommodate the wireless transmitter/preamp/microphone and/or piezo pickup 76.

Figure 25:
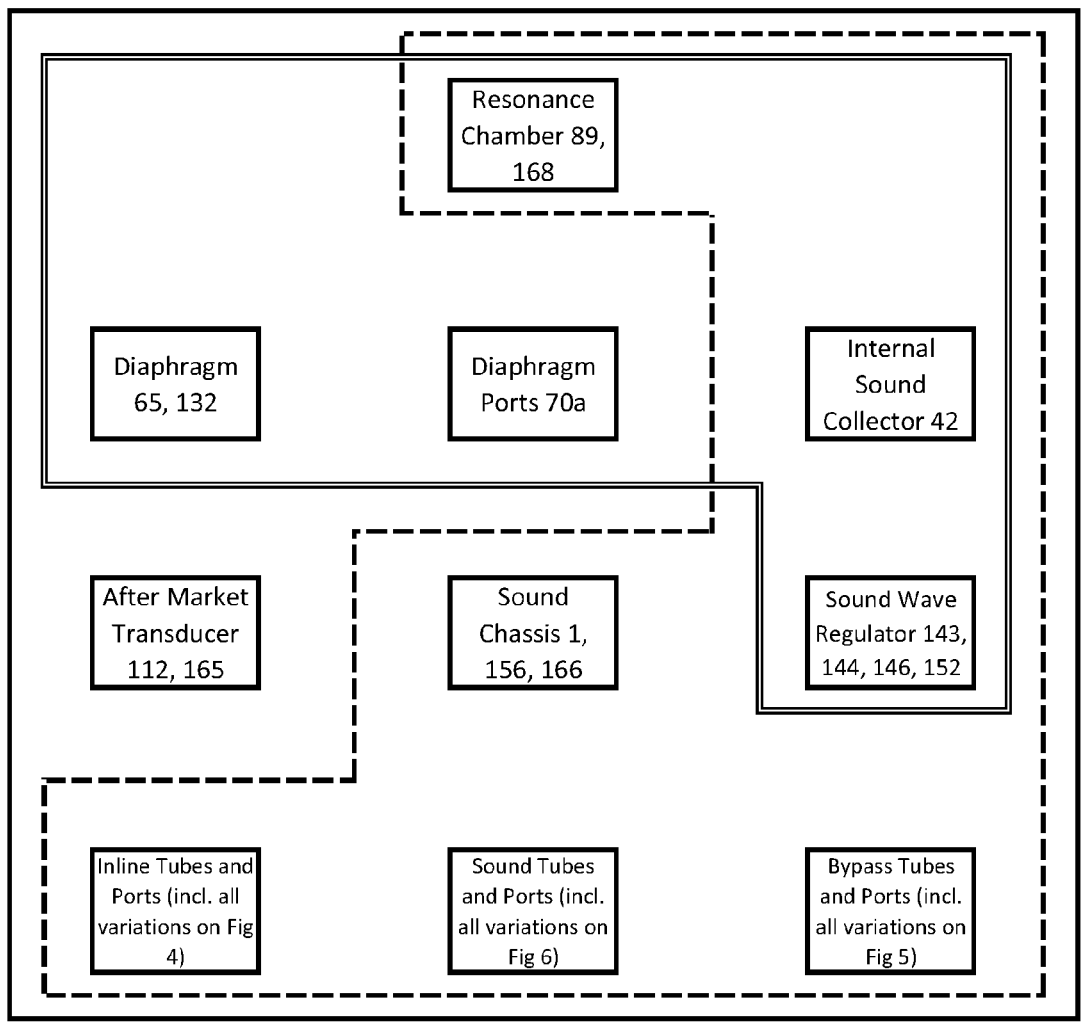
FIG. 25 is a representation of the interconnected systems of the sound processor.

Several embodiments of the present invention are directed to a mechanical processor housing a modular, adjustable, and interconnected set of systems for processing sound waves. In one embodiment, the three interconnected systems are the acoustic soundwave intake, resonance control, and output systems. Some embodiments of the present invention can operate as intended if, with the general exception of the resonance chamber, some of the components that make up an individual system are omitted or added. However, omitting an entire system may result in reduced or no functionality since as all three systems may operate optimally as an interconnected set as represented in FIG. 25.

Figure 26:
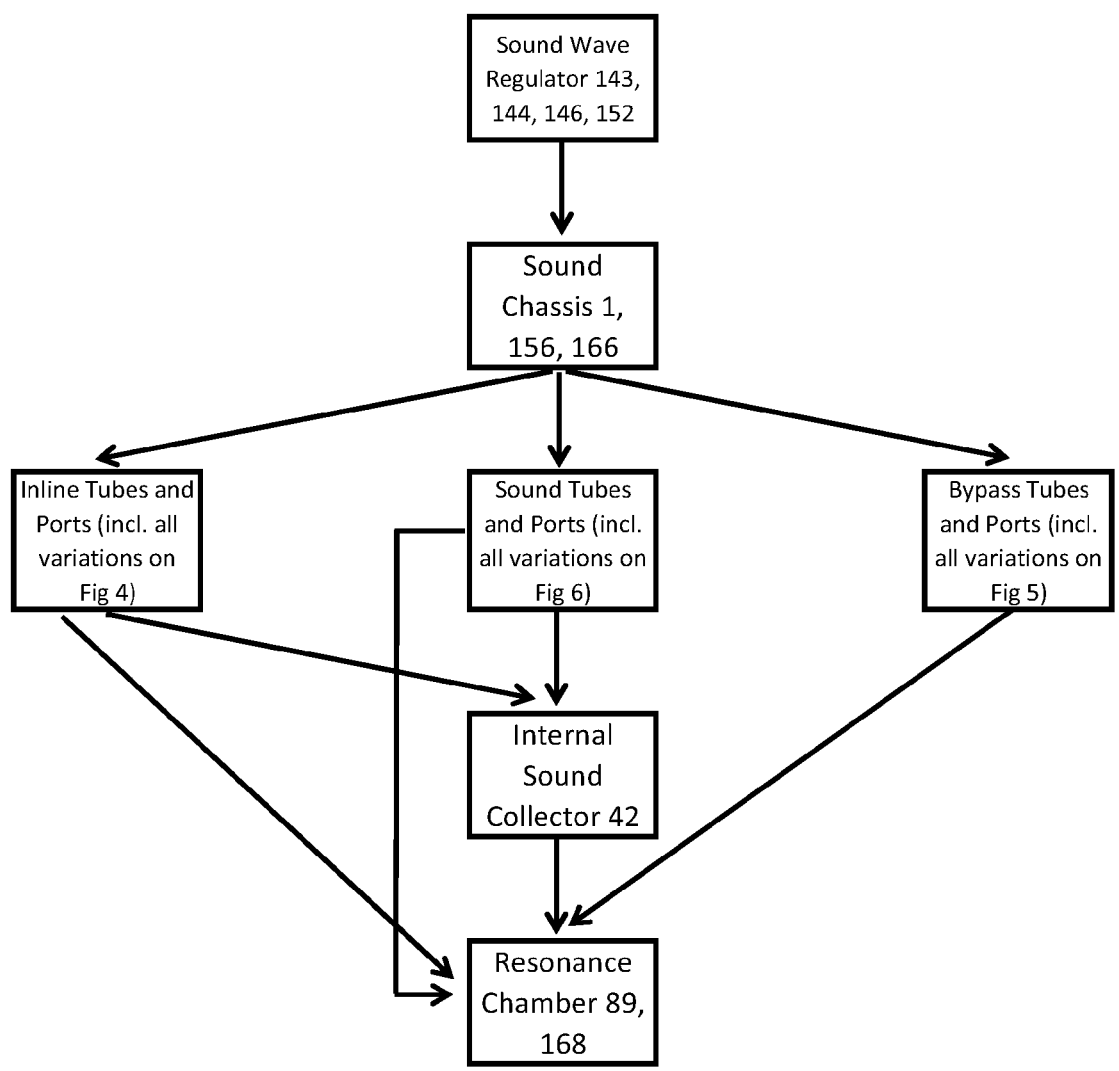
FIG. 26 is an acoustic soundwave intake system pathway.

FIG. 26 illustrates an acoustic soundwave intake system pathway, which is comprised of the sound wave regulator 143, 144, 146, 152, sound chassis 1, 156, 166, inline ports 13, sound ports 33, bypass ports 23, internal sound collector 42 and the resonance chamber 89, 168. As noted with the arrows in this figures, sound first enters the sound wave regulator 143, 144, 146, 152 and passes into the sound chassis 1, 156, 166. From there, the sound either enters the bypass ports 23 and then moves on to the resonance chamber 89, 168 or enters the inline ports 13 and sound ports 33, into the internal sound collector 42, and/or the resonance chamber 89, 168.

FIG. 27 illustrates an acoustic soundwave resonance control system pathway, which is comprised of the resonance chamber 89, 168, internal sound collector 42, diaphragm 69, 132, diaphragm ports 70a, 133 and the sound wave regulator 143, 144, 146, 152, which are all connected to each other so as to allow sound to pass between each element as depicted via the arrows of this application.

Figure 28:
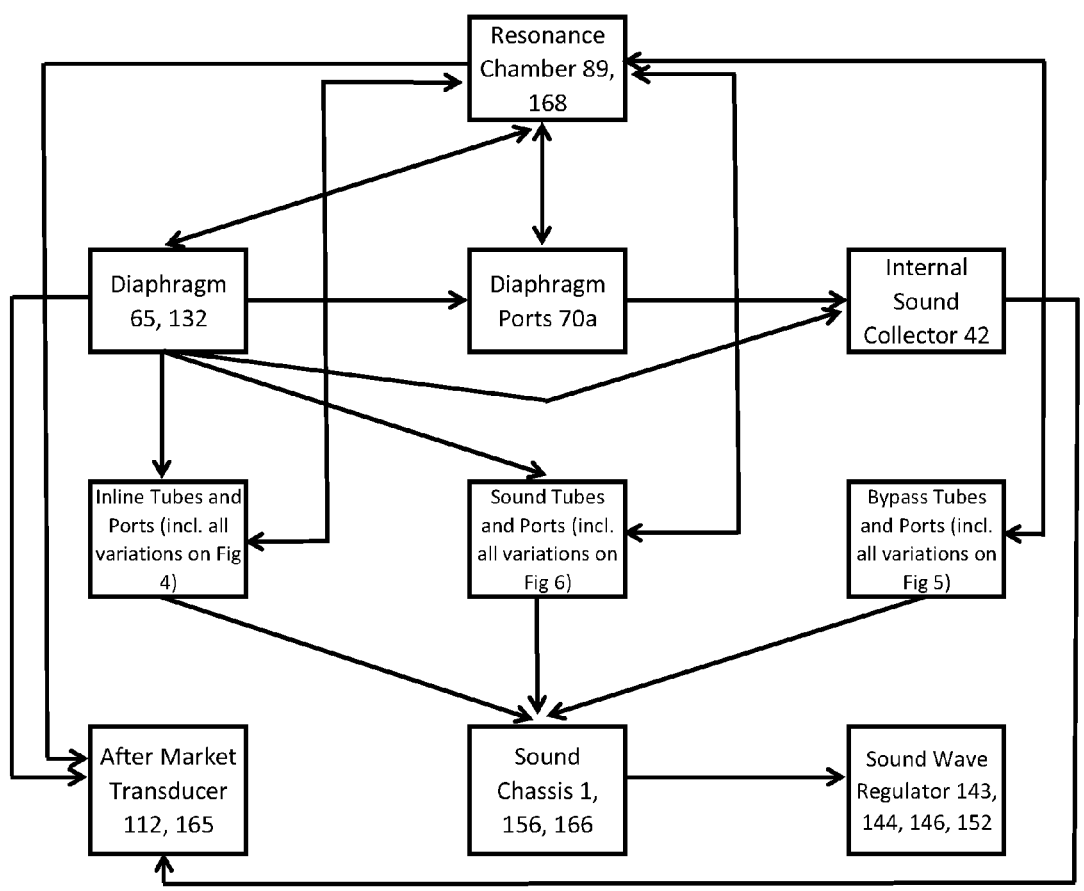
FIG. 28 is an acoustic soundwave output system pathway.

FIG. 28 illustrates an acoustic soundwave output system pathway, which is comprised of the resonance chamber 89, 168, diaphragm 69, 132, diaphragm ports 70a, 133 internal sound collector 42, inline ports 13, sound ports 33, bypass ports 23, after market transducer, sound wave regulator 143, 144, 146, 152 and the sound chassis 1, 156, 166, which are all connected to each other so as to allow sound to pass between each element as depicted via the arrows of this application. The pathway through the systems will vary depending on the input source, embodiment, accessories, and modular components used.

When used together as an interconnected set of systems, the acoustic soundwave intake system is analogous to a mixing board, as it has multiple inputs that can be mechanically adjusted. This system has the ability to reject incoming soundwaves by the shape of the sound chassis 1, 156, 166, the use of external deflectors 161, 162, the use and strategic placement of sound regulators 143, 144, 146, 152, which, depending on the type, will filter, deflect and compress the incoming soundwave. This is ideal to the overall process as it minimizes the ambient or predominant, unwanted sound waves and allows the processor to hone in on the desired sound waves. The inline tubes 12a are used to focus on an exact area of the sound source. This is achieved by pointing the inline tube ports 13 to the focal point and by selecting the proper diameter of tube, placement, number of side ports on the tube and length.

The diameter of the inline tube 12a (for example, shown in FIG. 4) determines which low, mid, or high frequencies will enter the system. A larger diameter (e.g., 1.0 inch opening) will allow more of the lower frequencies to be admitted through the tube whereas a smaller diameter (e.g., 0.25 inch opening) will cut out more of the lower frequencies. When using a small diameter tube, low sound waves will be minimized and a dominate higher end spectrum will be imported into the sound chassis 1, 156, 166. The side ports 21a and length of the inline tubes 12a determine other factors such as the ability to slow or speed up the sound waves, control when and at what point the selected sound wave enters the resonance control system.

The sound tubes 32a (for example, shown in FIG. 6) are selected in the same way as the inline tubes 12a. The main difference between them is the sound tubes 32a focus on the broad area of the desired sound source and the inline tubes 12a focus on an exact area of the desired sound source.

Using the two types of tubes 12a and 32a together in the same sound processing unit creates the ability for the processor to multi-task and distribute sound waves into the resonance chamber 89, 168 from different sound source locations at varying ratios, intensity, velocity, amplitude, and pressure. The incoming sound waves enter the acoustic soundwave resonance control system, which is the second stage of the sound processing system. Once the sound waves are initially selected and processed through the acoustic soundwave intake system, they will progress through one or multiple components of the acoustic resonance control system. The components of this system take on specific or multiple functions in which they can control the chamber environment. The components in this system can separate the sound signal further, sum specific or all frequencies to create a new wave form of the contributing signals. The acoustic soundwave resonance control system can also direct, diffuse, absorb, compress, expand, equalize, deflect, inject, delay, amplify and phase split the desired sound signals in the individual or combined wave shaping process.

Additional component accessories implemented in this stage can further incorporate effects such as acoustic echo, reverberation, tremolo and vibrato. The use of sound regulators 143, 144, 146, 152 diaphragms 69, 132 and selective types of materials play an important role in the input and output stages of the processing within the acoustic soundwave resonance control system because they can be adjusted to control and manage the interactions at the summing junctions.

Once the sound wave has been processed within the acoustic soundwave resonance control system, it enters the final stage in the acoustic soundwave output system. The acoustic soundwave output system uses the resonance chamber, summing junctions, after market transducers, if desired, and output passages to complete the cycle of sound processing. The summing areas can now be placed with one or a combination of aftermarket transducers like piezo pickups, microphones and/or acoustic transmission lines. The placement of these transducers and/or acoustic transmission lines in the center of the resonance chamber will sum all processed sound waves to one new sound wave at the placement point and can be transduced in that new state. Changing the placement point within the resonance chamber will yield the acoustical textures and reflections of the shape and components of the resonance chamber at the new placement point.

The placement of transducers and acoustic transmission lines in contact or very close to components, such as the chamber surface 163, diaphragms 69, 132, sound regulators 143, 144, 146, 152, sound boards 86, front and rear processor chassis 1, 156, 166 chassis ports 13, 23, 33 tubes 12a, 22a, 32a rotary chassis 51 and internal sound collectors 42, will transduce the close range signal and sum the sound waves into one signal or multiple individual signals. This creates many configurations for measuring, analyzing, mixing, amplifying and listening to the processed sound waves.

The linear, convex, ellipsoid, rotary and wireless designs are component variations but are not limited in shape, size, materials or a particular embodiment for the invention to work as designed. As such, the designs of the embodiments of the present invention can be used with a variety of hollow body musical instructions, such as an acoustic guitar, with microphones, with hearing aids, and similar devices that electrically function as a sound input device.

Figure 29:
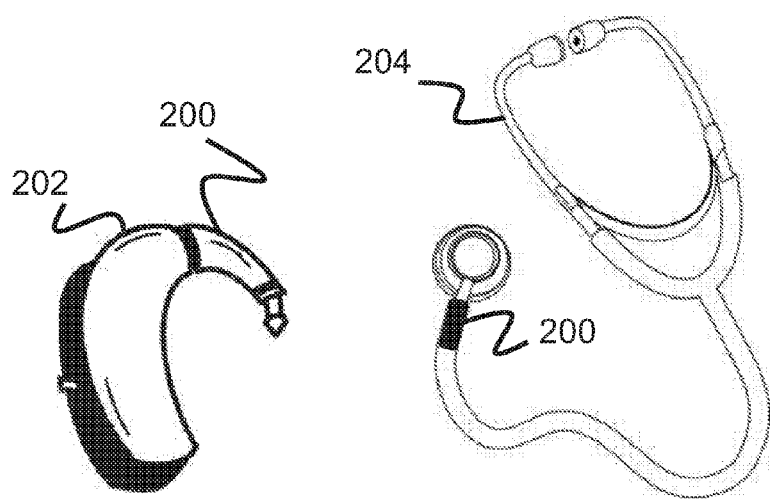
FIG. 29 illustrates a hearing aid and a stethoscope with a sound processor according to the present invention.

Although the preceding description contains significant detail, it should not be construed as limiting the scope of the invention but rather as providing illustrations of the potential embodiments of the invention. As an example, the complete modular system illustrated could take many different forms. Another alternative would be a square, elliptical, triangular or pyramid shaped processing device. In addition, the invention should not be limited in application to acoustic instruments. Using an interconnected modular, adjustable processor to pinpoint direction of sound, amplify, acoustically multi-process, measure, and transform sound within or outside of a resonance chamber has application in any industry that includes sound waves. Examples of applications for this invention are, but should not be limited to, recording, performing and field microphones, wind, brass and acoustic instruments, stethoscopes (e.g., stethoscope 204 with sound processor 200 in FIG. 29), surveillance microphones, exhaust systems, noise reduction, noise cancellation, ultrasound devices, speaker enclosures, scientific sound measuring, and hearing aids (e.g., hearing aid 202 with sound processor 200 in FIG. 29).

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An acoustic sound processor, comprising:
   an acoustic soundwave intake system comprising a sound chassis having a plurality of sound chassis openings;
   an acoustic soundwave resonance control system comprising a resonance chamber formed from a resonance chassis having a plurality of resonance chassis openings into said resonance chamber;
   a first plurality of tubes that are each connected to and opening at one of said first plurality of sound chassis openings and that are connected to and opening at one of said plurality of resonance chassis openings;
   at least one tube having a first end connected to and opening at one of said plurality of sound chassis openings and extending beyond said resonance chassis, such that a second end of said at least one tube bypasses said resonance chamber; and,
   an acoustic soundwave output system comprising a diaphragm positioned in proximity to said resonance chassis and on an opposite side of said resonance chassis than said sound chassis.

2. The acoustic sound processor of claim 1, wherein said second end of said at least one tube bypasses said diaphragm, creating a passage extending completely through said acoustic sound processor.

3. The acoustic sound processor of claim 1, wherein said acoustic sound processor has a cylindrical shape that is sized to fit within a sound hole to an acoustic instrument resonance chamber.

4. The acoustic sound processor of claim 1, wherein said plurality of resonance chassis openings further comprise at least one inline opening that is aligned such that said at least one inline opening is positioned to capture selected focal points produced by an acoustic instrument.

5. The acoustic sound processor of claim 4, wherein said plurality of resonance chassis openings further comprise at least one sound port opening having a diameter that is larger than said inline openings.

6. The acoustic sound processor of claim 1, wherein said sound processor is configured to fit over an electronic transducer.

7. The acoustic sound processor of claim 1, wherein said sound processor is integrated into a hearing aid.

8. The acoustic sound processor of claim 1, wherein said sound processor is integrated into a stethoscope.

9. The acoustic sound processor of claim 1, further comprising a vibrato chassis positioned between said resonance chassis and said diaphragm; said vibrato chassis comprising a rotary motor coupled to a blade positioned to periodically move over airflow openings of said vibrator chassis.

10. The acoustic sound processor of claim 1, further comprising a wireless chassis, including an electronic sound input device and a wireless transmitter connected to the electronic sound input device.

11. An acoustic sound processor, comprising:
   an acoustic soundwave intake system comprising a sound chassis having a plurality of sound chassis openings;
   an acoustic soundwave output system comprising a diaphragm positioned in proximity to said resonance chassis and within said sound chassis;
   an acoustic resonance control system comprising a resonance chamber formed between said sound chassis and said diaphragm;
   a first plurality of tubes that are each connected to and opening at one of said first plurality of sound chassis openings and into said resonance chamber;
   at least one pass through tube that connects to one of said first plurality of sound chassis openings and to said diaphragm, such that an interior of said diaphragm is in direct communication with an exterior of said sound chassis.

* * * * *